US 8,414,613 B2

(12) United States Patent
Huxel et al.

(10) Patent No.: US 8,414,613 B2
(45) Date of Patent: Apr. 9, 2013

(54) MEDICAL DEVICE AND PROCEDURE FOR ATTACHING TISSUE TO BONE

(75) Inventors: Shawn T. Huxel, Lawrenceville, NJ (US); David Gordon Levinsohn, San Diego, CA (US); Alan B. Miller, Jamison, PA (US)

(73) Assignee: Orthonoble Inc., Del Mar, CA (US)

( * ) Notice: Subject to any disclaimer, the term of this patent is extended or adjusted under 35 U.S.C. 154(b) by 0 days.

(21) Appl. No.: 12/297,530

(22) PCT Filed: Oct. 31, 2007

(86) PCT No.: PCT/US2007/023108
§ 371 (c)(1),
(2), (4) Date: Jul. 23, 2009

(87) PCT Pub. No.: WO2008/054814
PCT Pub. Date: May 8, 2008

(65) Prior Publication Data
US 2009/0312793 A1 Dec. 17, 2009

Related U.S. Application Data

(60) Provisional application No. 60/855,828, filed on Oct. 31, 2006, provisional application No. 60/855,831, filed on Oct. 31, 2006, provisional application No. 60/922,558, filed on Apr. 9, 2007.

(51) Int. Cl.
*A61B 17/04* (2006.01)
(52) U.S. Cl. .......... 606/232; 606/139
(58) Field of Classification Search .......... 606/139, 606/232, 104, 142, 144, 148, 151, 153, 191, 606/202, 213–216, 321, 323–327; 623/13.12, 623/13.14, 17.16
See application file for complete search history.

(56) References Cited

U.S. PATENT DOCUMENTS

| 4,870,957 | A | * | 10/1989 | Goble et al. .......... 623/13.12 |
|---|---|---|---|---|
| 5,258,016 | A | | 11/1993 | Dipoto et al. |
| 5,584,835 | A | | 12/1996 | Greenfield |
| 6,540,750 | B2 | | 4/2003 | Burkhart |
| 7,037,324 | B2 | | 5/2006 | Martinek |
| 7,585,311 | B2 | | 9/2009 | Green et al. |
| 2004/0138706 | A1 | | 7/2004 | Abrams et al. |
| 2005/0055052 | A1 | | 3/2005 | Lomardo et al. |
| 2005/0245932 | A1 | | 11/2005 | Fanton et al. |
| 2005/0251202 | A1 | | 11/2005 | Ewers et al. |

(Continued)

FOREIGN PATENT DOCUMENTS

| EP | 1588666 A2 | 10/2005 |
|---|---|---|
| WO | 0110312 | 2/2001 |

(Continued)

OTHER PUBLICATIONS

International Search Report dated Mar. 6, 2008.

(Continued)

*Primary Examiner* — Corrine M McDermott
*Assistant Examiner* — Gregory Anderson
(74) *Attorney, Agent, or Firm* — Saul Ewing LLP

(57) ABSTRACT

The invention pertains to medical devices for anchoring a suture engaged with soft tissue to a bone, the devices including tissue fastening medical devices, bone anchor medical devices, bone anchor driving tools and impactor tools, and procedures for using the same.

20 Claims, 31 Drawing Sheets

U.S. PATENT DOCUMENTS

| | | |
|---|---|---|
| 2006/0004364 A1 | 1/2006 | Green et al. |
| 2006/0041261 A1 | 2/2006 | Osypka |
| 2010/0179573 A1 | 7/2010 | Levinsohn et al. |

FOREIGN PATENT DOCUMENTS

| | | |
|---|---|---|
| WO | 02/11630 A1 | 2/2002 |
| WO | 2006/037131 A2 | 4/2006 |
| WO | 2006128092 A2 | 11/2006 |
| WO | 2008054814 | 5/2008 |

OTHER PUBLICATIONS

International Search Report and Written Opinion issued in PCT/US2011/029559, dated Aug. 31, 2011.

Extended European Search Report, dated Aug. 17, 2012, issued in corresponding European Application No. 07839900.3.

English translation of Office Action, dated Aug. 28, 2012, issued in corresponding Japanese Application No. 2009-535324.

* cited by examiner

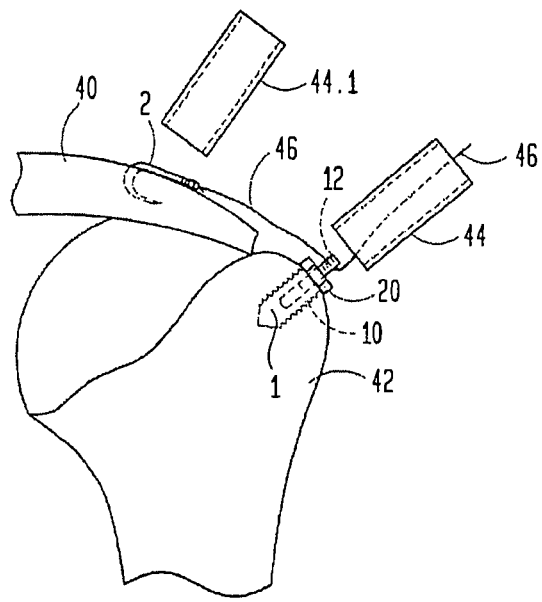
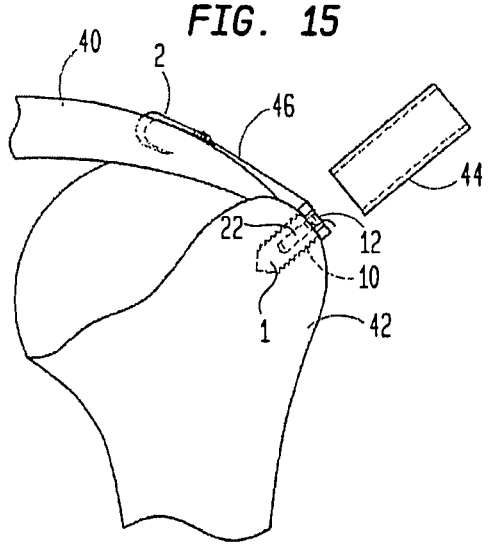

MEDICAL DEVICE AND PROCEDURE FOR ATTACHING TISSUE TO BONE

RELATED APPLICATIONS

This application claims priority to U.S. Provisional Patent Application Nos. 60/855,831 filed Oct. 31, 2006, 60/855,828 filed Oct. 31, 2006, and 60/922,558 filed Apr. 9, 2007, all of which are incorporated herein by reference in their entireties.

FIELD OF THE INVENTION

The invention relates to medical devices and procedures for attaching tissue to bone.

The invention relates particularly to medical devices and to medical procedures incorporating the use of the medical devices, that can be used in the repair of tendon tears, and the like, where repair requires the reattachment of soft tissue to skeletal structures, i.e. bones.

BACKGROUND OF THE INVENTION

Rotator cuff tears often require reattachment of soft tissue to skeletal structures and the explanation of the invention as hereinafter set out refers particularly to the repair of rotator cuff injuries, although it must be understood that the invention can be employed also in association with other like injuries where similar repair techniques are ordinarily employed or considered. The rotator cuff is the anatomical term given to a group of muscles and their tendons that act to move and stabilize the shoulder. These muscles extend from the scapula, i.e. the shoulder blade bone, and connect to the humerus, i.e. the upper arm, via their tendons, forming a cuff at the shoulder joint, thus serving to control different arm movements. A rotator cuff tear can result from a trauma to a shoulder or through wear and tear and be associated with one or more tendons becoming torn, leading to pain, shoulder instability and/or restricted arm movement.

Rotator cuff repair involves a surgeon reattaching each damaged tendon to the humerus. The conventional surgical process typically includes the steps of gaining access to the injured rotator cuff by making an incision in the shoulder and splitting the deltoid muscle and then removing scar tissue that has built up on each torn tendon. The surgeon then creates a trough at the top of the humerus and drills small holes through the bone, whereafter he sews the tendon to the bone with sutures passing through the holes. Other steps also may be associated with the process in order to deal with specific repair requirements. Following the process, the arm is incapacitated and healing is allowed to occur, which involves the reattachment of the tendons to the bone and which is generally a slow process.

Instead of passing sutures through holes drilled in the humerus for securing the tendon to the humerus, it is also known to use permanent anchors with sutures attached, inserted in the humerus, for this purpose.

More recently, arthroscopic surgery is being employed for rotator cuff repair. The surgery is performed through one or more small incisions. The surgeon observes the area of interest via a display screen which displays live images from a camera that is placed in a tube (cannula) passing through a small incision into the joint space. The instruments used are thin and are contained in separate cannulas that are inserted into the shoulder via separate small incisions. This arthroscopic surgery process includes placing anchor devices to which sutures are engaged for securing tendons to the humerus. In some techniques a pilot hole is required prior to placement of an anchor device. Each suture is passed through the tendon with a suture passing instrument. In most cases, all of the sutures are passed before tying. The sutures are then tied to anchor devices by the technique of arthroscopic knot tying. Various difficulties are associated with arthroscopic surgery as above envisaged.

The location of and the angle of a pilot hole for an anchor device is difficult to appreciate arthroscopically, rendering the location of anchor devices in their holes difficult.

The tying of sutures arthroscopically is very challenging.

Insofar as suture management is concerned, present techniques often require multiple sutures to be placed in position first and then to be tied to their anchor devices, often creating a "spider web" with entanglement of sutures and resulting in accidental pull-out of sutures and failure to recognize appropriate suture strands to be tied. Placing of sutures also presents difficulties insofar as multiple passes through the tendon are often required and snaring of suture portions by the soft tissue forming a tendon also can occur, resulting in difficulty in retrieving sutures into the portal of the equipment used.

SUMMARY OF THE INVENTION

In accordance with a first aspect of the invention, a tissue fastener device is provided for attachment of the soft tissue to bone, the tissue fastener device comprising a body that defines a shank portion and a hook formation extending from the shank portion, the shank portion defining a formation that permits fastening to bone with a fixation device such as a suture, pin, peg or a screw and the hook formation being configured to be engaged within soft tissue through manipulation of the body of the tissue fastener device.

In accordance with a second aspect of the invention, a procedure is provided for attaching soft tissue to bone with the aid of sutures including providing, through incision into the body, access to the soft tissue and to the bone to which it must be attached, providing a tissue fastener device comprising a body that defines a shank portion and a hook formation extending from the shank portion, the shank portion defining a formation that permits fastening to bone with a fixation device such as a suture, pin, peg or a screw and the hook formation being configured to be engaged within soft tissue through manipulation of the body, and, in the example of the fastener being a suture, tying the suture to the body of the tissue fastener device via the formation defined therefore by the shank portion, engaging each suture tied to a tissue fastener device with the soft tissue to be attached to a bone by engaging the hook formation of the tissue fastener device with the soft tissue, and anchoring each suture engaged with the soft tissue under tension to the bone.

In accordance with a third aspect of the invention, a bone anchor device is provided for anchoring at least one suture engaged with soft tissue to a bone comprising an anchor main body for insertion into a bone and a pin having a longitudinal axis and a passage transverse to the axis through which at least one suture can be passed, the anchor main body defining a receiving formation therein for receiving the pin, the pin being movable in the body between a first position that permits at least one suture to be relatively freely slid through the passage, tensioning the sutures attached to the soft tissue, and then moving the pin to a second position in which the at least one suture is relatively securely held. In accordance with fourth aspect of the invention, a procedure is provided for anchoring sutures engaged with soft tissue to a bone including providing, through incision into the body, access to the bone, providing for a suture engaged with the soft tissue, providing a bone anchor device comprising a substantially cylindrical body for insertion into a bone and a pin having a longitudinal axis and a passage transverse to the axis through which a suture can be threaded, the cylindrical body defining a receiving formation therein for receiving the pin with a suture threaded through the passage of the pin, the pin being deployable into a locking position in which a suture passing through the formation is securely held between the cylindrical body and the pin, affixing the body of each bone anchor device into the bone, and passing each suture engaged with the soft tissue through the passage defined in the pin of the bone anchor device, and, while holding the suture under tension, deploying the pin into its locking position in the receiving formation of the cylindrical body, for anchoring the suture and thereby the soft tissue engaged by the suture to the bone.

DESCRIPTION OF THE DRAWINGS

Further features of the various aspects of the invention are described hereinafter with reference to the accompanying diagrammatic drawings. In the drawings:

FIGS. 13 to 15 schematically illustrate steps associated with a second medical procedure for attaching soft tissue to bone and which includes the use of the bone anchor device of FIGS. 1-4 and the tissue fastener device of FIGS. 5-7;

DETAILED DESCRIPTION

First Set of Exemplary Embodiments

Figure 1:
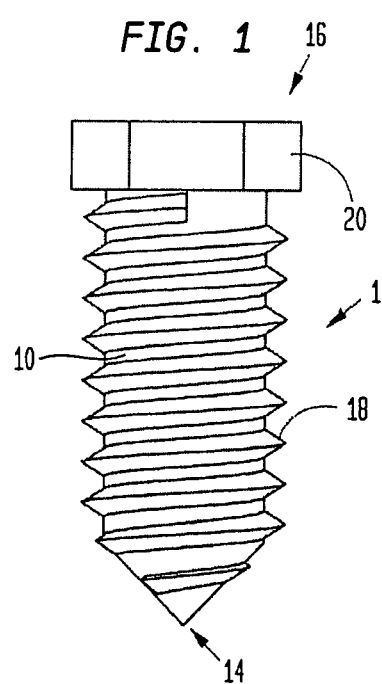
FIG. 1 shows a side view of a anchor main body forming a part of a first embodiment of a bone anchor device for anchoring a suture engaged with soft tissue to a bone in accordance with the invention.
Figure 2:
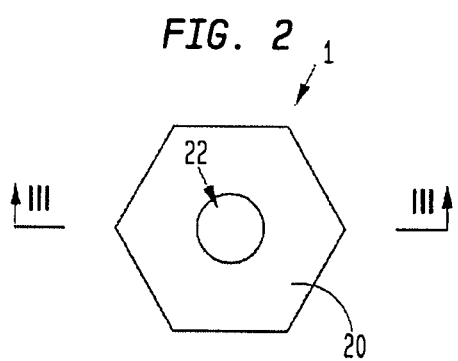
FIG. 2 shows a top view of the anchor main body of FIG. 1.
Figure 3:
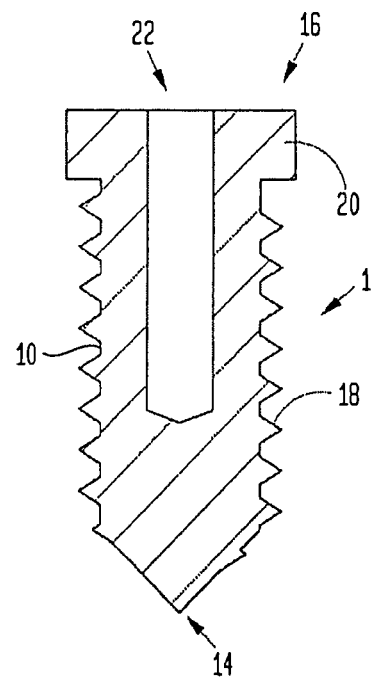
FIG. 3 shows a cross-sectional side view of the anchor main body of FIG. 1, along line III-III of FIG. 2.
Figure 4:
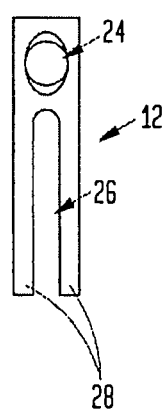
FIG. 4 shows a side view of an eyelet pin forming a further part of the first embodiment of the bone anchor device of which the anchor main body of FIG. 1 forms a part, the eyelet pin being configured to cooperate with the anchor main body of FIG. 1.
Figure 5:
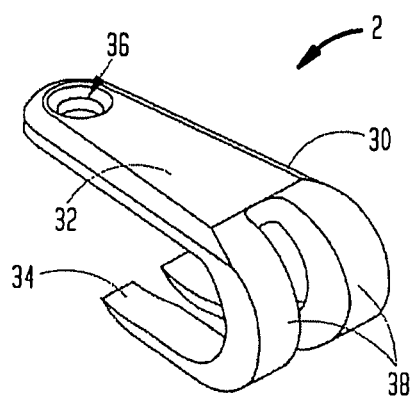
FIG. 5 shows a perspective view of a tissue fastener device for use in a medical procedure associated with the use of a medical device including the anchor main body of FIG. 1 and the eyelet pin of FIG. 4.
Figure 6:
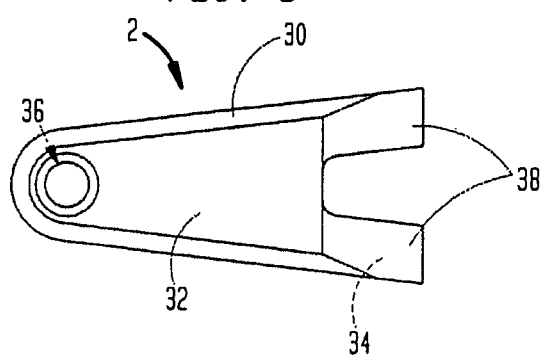
FIG. 6 shows a top view of the tissue fastener medical device of FIG. 5.
Figure 7:
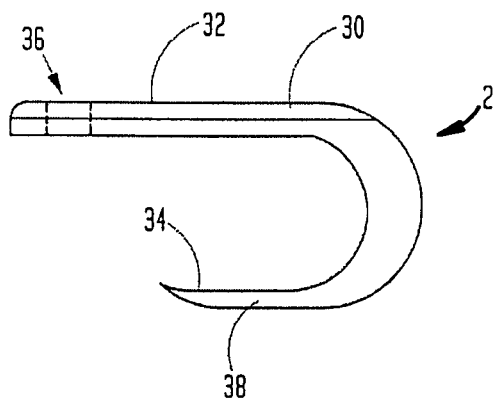
FIG. 7 shows a side view of the tissue fastener medical device of FIG. 5.

A medical system in accordance with a first embodiment of the present invention comprises two primary components, namely, a bone anchor device 1 as shown in FIGS. 1-4 and a tissue fastener device 2 as shown in FIGS. 5-7.

Referring initially to FIGS. 1-4, a bone anchor device 1 in accordance with the invention is shown for anchoring a suture that is engaged with soft tissue to a bone. It includes a substantially cylindrical body 10 and an eyelet pin 12. Both the anchor main body 10 and the eyelet pin 12 may be formed of a biocompatible material, such as of a type already commonly used within the body of a person, e.g., a metal or metal alloy such as titanium, stainless steel or cobalt-chrome alloys; a suitable polymeric material that is nonabsorbable, such as polyethylene, poly-ether-ether-ketone (PEEK), poly-ether-aryl-ketone (PEAK); a resorbable polymer selected from homopolymers, copolymers and blends of polylactide, polyglycolide, polyparadioxanone, polytrimethylene carbonate or polycaprolactone; or composites of the aforementioned with biocompatible inorganic substances such as carbon, hydroxyapatite, beta tricalcium phosphate, other calcium phosphate ceramics or calcium sulfate.

The anchor main body 10 defines a leading end 14 and a trailing end 16 and an external formation such as a thread 18 extending externally along the length thereof from its leading end towards its trailing end to help secure the body 10 to bone. At its trailing end 16, the body 10 defines a head formation 20, the head formation 20 being geometrically profiled to permit engagement with a screw driver-type tool, for screwing the body into a bone. The body 10 also defines a receiving formation therein that is in the form of a cylindrical blind bore 22, the receiving formation 22 being particularly configured to frictionally receive the eyelet pin 12 therein.

The eyelet pin 12 could be formed of the same material as the anchor main body 10, the pin comprising a substantially cylindrical pin that defines a passage 24 therethrough near a proximal end thereof and a longitudinal slot 26 that extends therein from the distal end toward the proximal end near which the passage 24 is defined. The pin thus defines two legs 28 on opposite sides of the slot 26. The pin 12 is particularly configured to be securely locatable within the receiving formation 22 defined by the anchor main body 10 by a friction fit, inherent resilient deformability of the material forming the pin and the configuration of the slot serving to enhance required location of the pin within the receiving formation 22 defined by the body 10. The exact configurations of the anchor main body and of the pin are greatly variable.

FIGS. 5-7 illustrate a tissue fastener device 2 for use in conjunction with the bone anchor device 1 in a medical process. The tissue fastener device 2 comprises a body 30 that defines a shank portion 32 and a hook formation 34, the shank portion 32 having a hole 36 defined therein near the free end thereof. Generally, the configuration of the hook formation is greatly variable, the hook formation 34 in this case being defined by two spaced apart prongs 38, the free ends of the prongs extending substantially parallel to the shank portion 32. The hole 36 permits a fastener such as a length of suture or a screw to be attached to the body 30, whereas the free end of the shank portion 32, possibly in conjunction with the location of the hole 36, is configured to be engageable with an applicator tool whereby the body can be manipulated for engaging soft tissue via the hook formation 34, within a medical procedure, as is explained in more detail hereafter.

Insofar as the tissue fastener 2 is configured for use in an arthroscopic procedure, the end region of the shank portion 32 of the body 30 where the hole 36 is defined is configured to engage an engagement formation of an applicator tool, the applicator tool providing for manipulation of the tissue fastener device 2 for engaging soft tissue, particularly via a cannula located in an incision in a body of a person in a location where it provides access to the location where the tissue fastener device 2 must be engaged with soft tissue. Although not essential, it is envisaged that such an applicator tool can be cannulated to provide for a suture to pass through the cannula, thus to provide for the free end of a suture tied to the tissue fastener device 2 to remain conveniently accessible externally of the body of a person following engagement of the device with soft tissue, as is described in more detail hereafter.

It must be understood that a specific arthroscopic applicator tool will be provided for use with the tissue fastener device 2 and/or that the tissue fastener device 2, as described, may require modification for cooperating with a particular tool, in order to facilitate its use as hereafter described.

The tissue fastener device 2 may be formed of a metal material of a type already used for medical devices used within the body of a person, e.g., a metal or metal alloy such as titanium, stainless steel and cobalt-chrome alloys; a suitable polymeric material that is nonabsorbable, such as polyethylene, poly-ether-ether-ketone (PEEK), poly-ether-aryl-ketone (PEAK); a resorbable polymer selected from homopolymers, copolymers and blends of polylactide, polyglycolide, polyparadioxanone, polytrimethylene carbonate or polycaprolactone; or composites of the aforementioned with biocompatible inorganic substances such as carbon, hydroxyapatite, beta tricalcium phosphate, other calcium phosphate ceramics or calcium sulfate.

First Set of Exemplary Surgical Procedures

The bone anchor device 1 and the tissue fastener device 2 are configured particularly for use in a medical procedure for anchoring sutures engaged with soft tissue to a bone, thereby attaching the soft tissue to the bone. Sutures engaged with soft tissue to be anchored to a bone within the procedure may be engaged with the soft tissue by any known method, although for the first procedure described hereafter with reference to FIGS. 8 to 12, the sutures are separately tied to the tissue fastener devices 2 of FIGS. 5 to 7 that are engaged with soft tissue through the engagement of the hook formations 34 of the devices 2 with the soft tissue.

The procedure as above envisaged is typically applied in association with rotator cuff repair and is hereinafter described in association with such a repair procedure, although it must be appreciated that the medical devices 1 and 2 as above described also can be used in association with other procedures that require soft tissue to be attached to or re-attached to skeletal structures, i.e., to bone.

Rotator cuff repair is required where a tendon that acts to stabilize the shoulder has torn and thus is to be reattached to the humerus, i.e. the upper arm bone, thereby to re-establish normal arm movement. As envisaged above, such repair ordinarily involves a surgeon gaining access to the tendon and the humerus through incision, engaging sutures to the tendon in a conventional manner, and then sewing the sutures to the humerus via holes formed therein for anchoring to the humerus. Anchoring to the humerus by tying the sutures to anchor devices located in the humerus also is known. The same principles apply also to the procedure that is explained hereafter with particular reference to FIGS. 8 to 12 and that is associated with the use of the medical devices 1 and 2 described above.

Referring now to FIGS. 8 to 12 of the drawings, the rotator cuff repair procedure illustrated particularly is an arthroscopic procedure which includes, as a first step, providing access to the damaged tendon 40 and the humerus 42 by forming one or more incisions in the shoulder region and inserting a cannula 44 in each incision.

The general procedure in association with the location of cannulas 44, which can provide access to required locations to permit the repair procedure to be carried out, is already well known and is thus not described further herein. Each cannula located in an incision provides access to locations where the procedure must be performed, particularly also for arthroscopic tools or instruments that can serve to suitably manipulate the medical devices above described, within the procedure. The configuration of such arthroscopic tools or instruments are generally well known, but insofar as existing tools or instruments may not be specifically configured to accommodate manipulation of the medical devices described, existing tools or implements may be suitably adapted or new tools or instruments may be designed, using known principles, in order to facilitate the procedure.

Figure 8:
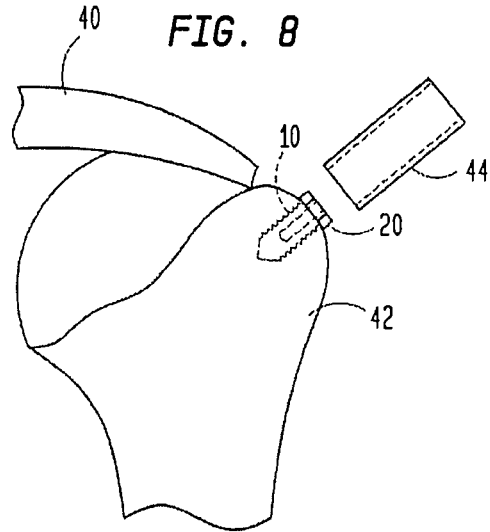
FIGS. 8 to 12 schematically illustrate steps associated with a first medical procedure for attaching soft tissue to bone and which includes the use of the bone anchor device FIGS. 1-4 and the tissue fastener device of FIGS. 5-7.

With reference to FIG. 8, the first step in the arthroscopic procedure for performing a rotator cuff repair following the location of a cannula that provides access to the humerus 42 provides for the anchor main body 10 of the bone anchor device 1 to be screwed into the humerus 42 in a desired anchoring location. An arthroscopic screw driver engaging the head formation 16 of the anchor main body 10 is used for this purpose, the typical location of the anchor main body being shown in FIG. 8 of the drawings, which also illustrates the head formation 16 of the body that remains exposed externally of the humerus 42. For a medical device having an anchor main body without a head formation, this exposure may not occur. It must be understood in relation to this procedure that a further cannula accommodates an instrument carrying a camera, enabling a surgeon to observe the area of interest, particularly via live images displayed on a display screen. Additional anchor main bodies 10 that can form anchors for sutures will be similarly screwed into the humerus 42 before proceeding with the next step in the procedure.

Figure 9:
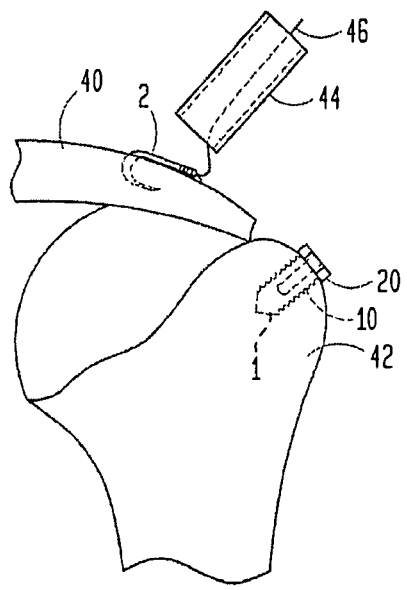

With reference to FIG. 9, the next step in the procedure provides for tying of individual sutures 46 to the respective bodies 30 of the tissue fastener devices 2. Alternately, the sutures can be pre-tied to the fastener, or simply looped through hole 36. Next, the hook formation 34 defined by each body is fastened to, under arthroscopic visualization, the tendon 40 being repaired, particularly again via a suitably located cannula 44 and with the aid of a suitable instrument that permits manipulation of the body 30 to provide for engagement of the hook formation 34 with the tendon. The suture 46 tied to each body 30 optionally may extend centrally through the applicator tool utilized, the free end of the suture thus remaining accessible externally of the person's body. A suture 46 extending from a body 30 and via a cannula to a location externally of the body is illustrated. The number of sutures engaged with the tendon 40 for its repair clearly is determined by the extent of damage to the tendon.

Figure 10:
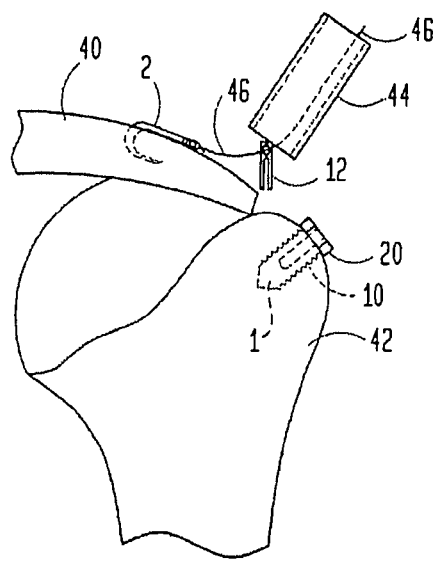
Figure 11:
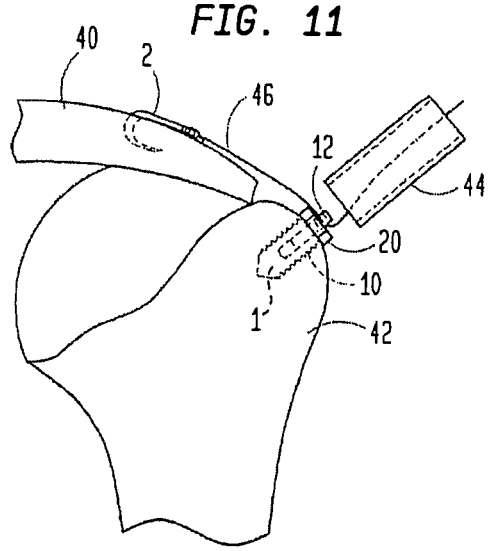
Figure 12:
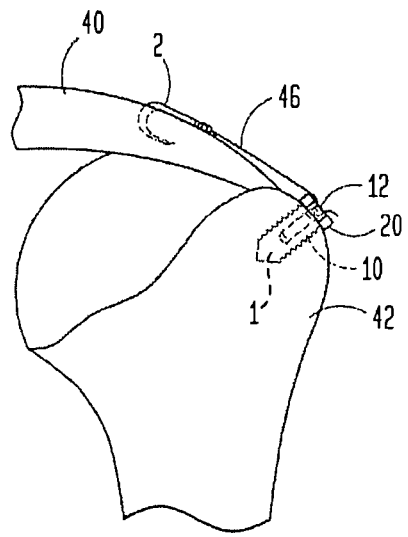

The procedure thus requires anchoring of the sutures 46 to anchor main bodies 10 via eyelet pins 12, and in this regard it must be understood that each anchor main body and its associated eyelet pin may serve to anchor either a single suture or two or more sutures with respect thereto. With reference to FIG. 10, this anchoring procedure includes, for each suture 46, threading the suture through the passage 24 defined in an eyelet pin 12, which can be done externally of the body, following which through manipulation of the eyelet pin by means of a suitable arthroscopic applicator tool such as the impactor tool shown in FIGS. 46-48 and described later, the eyelet pin is inserted through an appropriate cannula and partially inserted into the receiving formation 22 of an anchor main body 10 and the free end of the suture is pulled up through the cannula adjacent the bone anchor device 1, thus providing the configuration shown in FIG. 11. Thereafter, with reference to FIG. 12, by applying tension to the suture 46, the tendon 40 is pulled toward and against the humerus 42 from which it has been torn, thus to effectively place the tendon in abutment with the humerus in a configuration in which re-attachment with the humerus is permitted. While retaining the tension in the suture 46, the eyelet pin is further displaced into the receiving formation 22 of the anchor main body 10, particularly to the extent that the entire eyelet pin is located in the receiving formation 22. This can be achieved by impacting under arthroscopic visualization of the eyelet pin with a suitable impactor tool, such as that shown in FIGS. 46-48 and described later herein, extending through the cannula 44 and a mallet, the suture 46 being effectively anchored to the anchor main body by being clamped between the anchor main body and the pin. The free end segment of each suture can then be suitably cut-off. Normal finishing procedures associated with arthroscopic surgery can then be performed in order to finally complete the procedure.

Second Set of Exemplary Surgical Procedures

Figure 13:
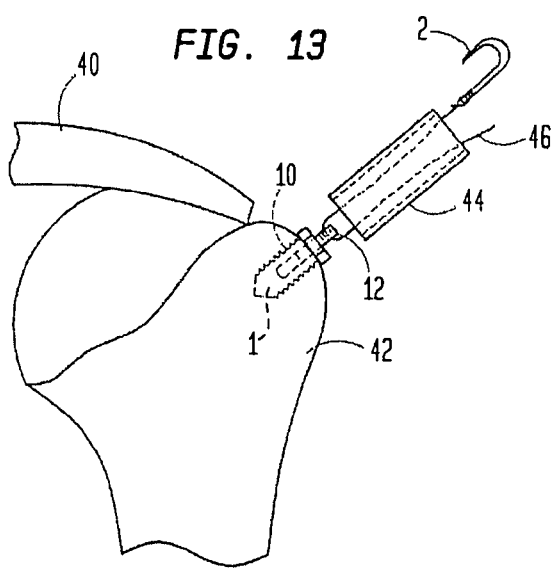

Referring now to FIGS. 13 to 15 of the drawings, a variation of the rotator cuff repair procedure as described with reference to FIGS. 8 to 12 of the drawings, is illustrated. In these Figures, like parts are designated by the same reference numerals as before. The procedure is again an arthroscopic procedure which includes, as a first step; providing access to the damaged tendon 40 and the humerus 42 by forming one or more incisions in the shoulder region and, usually, inserting a cannula in each incision. The same considerations in relation to the location of cannulas apply.

In this case, a bone anchor device 1 (including an anchor main body 10 and an eyelet pin 12) is provided in combination with at least one suture 46, threaded through the passage defined at one end of the eyelet pin 12, and a tissue fastener device 2, tied to the suture. The eyelet pin 12 is partially inserted in the receiving formation defined therefore in the anchor main body 10, free displacement of the suture 46 still being permitted.

With a cannula 44 being located that provides access to the humerus 42, the anchor main body 10 of the medical device is again screwed into the humerus in a desired anchoring location. This is achieved in the same way as before and provides the configuration shown in FIG. 13, in which the eyelet pin 12, suture 46 and body 30 are located as shown.

With reference to FIG. 14, the next step in the procedure provides for the suture 46 to be attached to the tendon 40 by engagement of the hook formation defined by the tissue fastener device 2 with the tendon, particularly with the aid of a suitable arthroscopic tool operated via the cannula 44.1. Instead of attachment of a suture to a tendon 40 with the aid of a tissue fastener device 2, the suture alternately can be "tied" to the tendon with the aid of a suitable suture passing instrument (not shown). Insofar as this form of attachment of a suture to a tendon is conventional and well known, it is not described or illustrated in more detail herein.

With reference to FIG. 15, with the suture 46 attached to the tendon 40, tension can be applied to the suture for displacing the tendon into its required "repair position" with respect to the humerus 42, following which the eyelet pin 12 is displaced into its fully inserted (or closed) position in its receiving formation 22 defined by the anchor main body 10, thus providing for anchoring of the suture 46 to the humerus. Following completion, the excess suture is cut-off.

It will be understood that both the above described procedures can be altered in various different respects. For example, for the procedure described with reference to FIGS. 8 to 12, it is envisaged that an eyelet pin can be partially inserted (in the open state) in an anchor main body without a suture threaded therethrough, whereafter the suture can be attached to the tendon to be repaired before being threaded through the passage 24 in the eyelet pin 12 and being anchored in position by the full insertion of the eyelet pin in its receiving formation. It must be understood in this regard that the exact procedure followed will be determined by individual procedure requirements and also the nature of the procedure which requires anchoring of sutures to bone with the aid of a medical device.

Some of the benefits associated with the use of a tissue fastener device in accordance with the invention within a medical procedure are explained hereafter particularly in relation to a rotator cuff procedure as above described, although it must be understood that some or all of these benefits may be associated also with other procedures as will be clearly apparent.

The known state-of-the-art procedures usually require placement of all sutures through the rotator cuff prior to securing of the sutures to the bone. This is necessary because the sutures are deployed into the rotator cuff tissue by a device that penetrates the full thickness of the cuff tissue; however, placement of a suture through the full thickness of the cuff tissue after a previous suture has already been secured to the bone, will potentially weaken or even disrupt the previous suture fixation. This problem cannot be resolved by moving the point of suture penetration further away from the preceding suture penetration point, as this will result in less secure fixation. One of the principle goals of rotator cuff repair is to recreate the anatomical footprint of the tendon's attachment via secure fixation and, for the reasons explained, this goal will be compromised by a "tie-as-you-go" method. It will be understood by those skilled in the art that the smaller the tear within the tendon, the less room there will be for safely placing a following suture through the torn tissue of the tendon without disrupting or weakening the prior-located suture(s).

As such, by facilitating a "tie/secure-as-you-go" procedure, the above problem of suture management is largely resolved and this is in fact achieved with the use of the tissue fastener devices of the invention, which permit "tie/secure-as-you-go" procedures. Also because the state-of-the-art procedures for the reasons explained, require multiple sutures to be engaged with rotator cuff tissue before anchoring thereof to bone, suture management of untied multiple suture strands is a major technical challenge in state-of-the-art arthroscopic rotator cuff repair. The problems intensify as the number of sutures are placed in position, a maze of sutures often leading to inadvertent tying of incorrect suture pairs, failure to find sutures in the procedure field, inadvertent release of sutures from their anchors and tangling of sutures around instruments and among other sutures and soft tissues. This suture management within the rotator cuff procedure above described and with the aid of the medical devices of the invention is greatly facilitated.

Still further, upon completion of a rotator cuff repair as envisaged, there are occasionally areas where the tendon is not adequately tensioned and not adequately laying on bone. For the reasons mentioned above, a surgeon cannot use a state-of-the-art suture passing instrument to augment the repair. However, with the use of the tissue fastener device 2 of the invention, a surgeon will have a simple option of augmenting and thereby to fine tune a repair without risking the existing repair sutures.

It is also known for suture passing devices to be used for deploying sutures into the rotator cuff. With the use of these devices there are several steps involved in the process, with each step being exposed to technical difficulties. These steps particularly involve the loading of sutures outside the portal defined by a cannula, grabbing the tendon in the jaws of the suture passing device arthroscopically, deploying the sutures arthroscopically, withdrawing the suture-passing device, and then retrieving the sutures into a portal. Alternately, cannulated suture shuttling and penetrating devices also are commonly used that involve several complex steps. Specifically, first the rotator cuff is pierced with the device. This is technically difficult, and to facilitate the procedure, devices that have various curves and or twists have been designed. Then, typically, a suture or wire (pullthrough stitch) is advanced through the cannulated shuttling device. This wire or suture is then retrieved into a separate cannula. Then, the suture to be used in the rotator cuff repair is placed through a loop or penetrating device in the pull-through stitch and pulled (shuttled) through the tendon. These complex processes are eliminated with the use of the tissue fastener device 2 of the invention, which affords a surgeon a simple method of attachment of suture to the tendon.

Third Set of Exemplary Surgical Procedures

Figure 16:
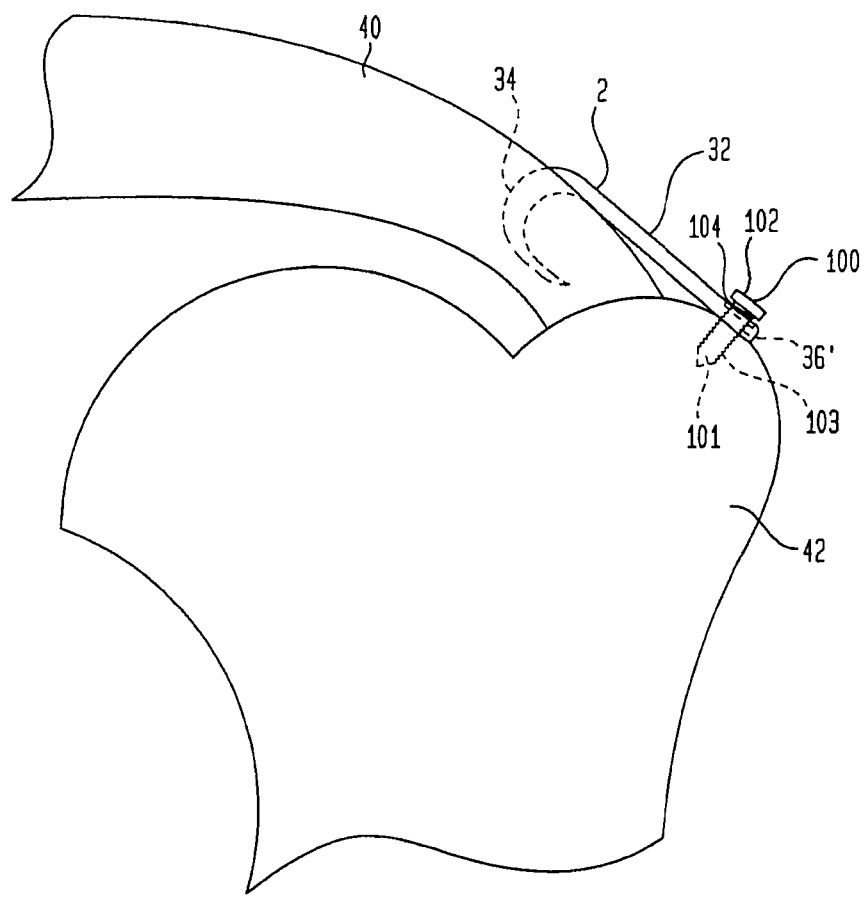
FIG. 16 illustrates schematically a third procedure for attaching soft tissue to bone and which includes the use of the tissue fastener device of FIG. 5.

FIG. 16 illustrates an alternative surgical procedure utilizing a tissue fastener such as tissue fastener 2 in accordance with the present invention that completely eliminates the use of sutures in any form. In this embodiment, a tissue fastener device has essentially the same basic components of the tissue fastener device 2 shown in FIGS. 5-7, including a shank portion 32, a hook formation 34, and a hole 36'. Instead of threading a suture through the hole 36', a bone anchor 100 is passed through the hole and screwed or otherwise inserted into the bone. The bone anchor 100 may be a simple bone screw with a threaded shaft 101 smaller in diameter than the diameter of the hole 36' in the tissue fastener device 2 and a head 102 with a diameter greater than that of the hole 36'.

The hole 36' may be counterbored (not shown) so that the head 102 of the screw 100 will be substantially flush with the surface of the shank portion 34 of the tissue fastener device 2. The screw may be polyaxial. For instance, the hole in the tissue fastener device may be spherical and the screw may have a mating spherical head so that the screw can pivot about the interface between the spherical head and the spherical seat in the hole through a defined cone of freedom. In one embodiment, the spherical head and/or the spherical seat in the hole may have ridges or other formations for interlocking with each other to generate a stronger grip between the screw head and the hole. The ridges may be plastically deformable when the screw is forced down into the seat to provide even stronger gripping there between.

In order to even further increase rigidity and help prevent backout of the bone screw 100, a mechanism to directly fixedly attach the screw 100 to the hole 36 in the tissue fastener device 2 (rather than just trapping the shank 32 of the tissue fastener device 2 between the head 102 of the screw 100 and the bone surface) may be additionally provided. For instance, hole 36' may be internally threaded so that, when screw 100 is screwed into the bone, it also threadedly engages and becomes directly fixed to the tissue fastener device 2, not only the bone 42. In a preferred embodiment of this feature, the threads 104 on the screw 100 for engaging the hole 36' are different than the threads 103 on the screw 100 for engaging the bone (since thread formations most suitable for threading into bone are different than thread formations most suitable for mating contact in a pre-threaded hole). In such an embodiment, the proximal portion of the shank of the screw 100 would bear threads 104 adapted for engaging the threads in the hole 36' and the distal portion of the shank of the bone screw 100 would bear threads adapted for engaging bone.

The tissue fastener device 2 may be engaged with the soft tissue 40 in the usual fashion as discussed above in connection with FIG. 9.

Thereafter, a suitable surgical tool can be inserted through a cannula that can guide the tissue fastener to a position such that the hole 36 is positioned above the desired location on the bone for the screw 100 to be inserted. The bone screw 100 is then inserted through a cannula (not shown) into the hole 36 and screwed into the bone using a suitable driver (not shown) in order to attached the tissue fastener 2 directly to the bone without the use of sutures.

In an alternate embodiment of the tissue fastener device, the shank may include more than one hole so that the tissue fastener device can attached to the bone using multiple screws, pegs, tacks, or other bone fastening devices.

Fourth Set of Exemplary Surgical Procedures

Figure 17:
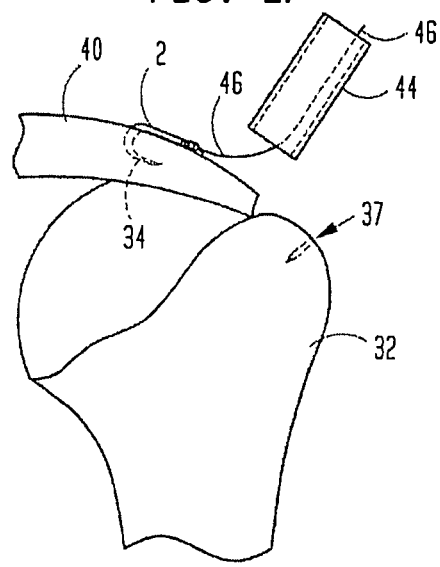
FIGS. 17 and 18 illustrate schematically the steps associated with a fourth procedure for attaching soft tissue to bone and which includes the use of the tissue fastener device of FIG. 5, a suture, and a conventional bone anchor.
Figure 18:
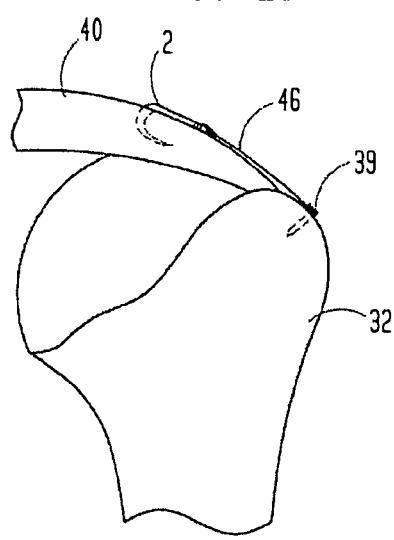

FIGS. 17 and 18 illustrate a further arthroscopic procedure for engaging a suture with soft tissue using the tissue fastener device 2 in conjunction with a conventional bone anchor 39.

Insofar as the procedure hereafter described is an arthroscopic procedure, the repair procedure is initiated by locating cannulas 44 (only one shown) in incisions that are positioned so that access is provided to the tendon 40 and the humerus 42 to which the tendon is to be attached, this access particularly accommodating the use of arthroscopic tools. The location of cannulas 44 and normal preparation in relation to a repair is conventional and, as such, is not described further herein.

Particularly, within an arthroscopic procedure as envisaged, the first step in the procedure typically involves the formation of a pilot hole 37 in the humerus 42 in a location where sutures must be anchored to the humerus. The pilot hole 37 is formed arthroscopically with the aid of a suitable tool that facilitates this. The pilot hole 37 particularly is formed to receive an anchoring device 39 therein, particularly a device to which sutures can be tied or otherwise secured for effective anchoring of the sutures to the humerus. The mode of location of an anchoring device is variable and is determined by the type of anchoring device involved, it being possible, for example, to locate an anchoring device without the requirement of first forming a drill hole.

Each suture 46 (there may be one or more) to be engaged with the tendon 40 and anchored to the anchoring device 39 to be located in the pilot hole 37 is then tied to a separate tissue fastener device 2, particularly via the hole 36 defined in the body 30 thereof. Thereafter, each body 2 is operatively engaged with an applicator tool that is configured to permit engagement of the tendon 40 by the tissue fastener device 2 via its hook formation 34, in the configuration as shown in FIG. 17. It will be understood that, when so engaged, the suture 46 tied to the device 2 will extend from the person's body via the cannula 44 through which access to the tendon is provided, the free end of the suture thus being easily "controllable".

With each suture 46 (only one shown) engaged with the tendon 40, each suture is tied under tension to an anchoring device 39 that is then located in the pilot hole 37 provided therefore. Insofar as this anchoring procedure is already known and insofar as it does not form a part of the present invention, this is not described further herein. The above procedure is performed for each further anchoring device to be used and the sutures to be anchored thereto.

Second Set of Exemplary Embodiments

Figure 19:
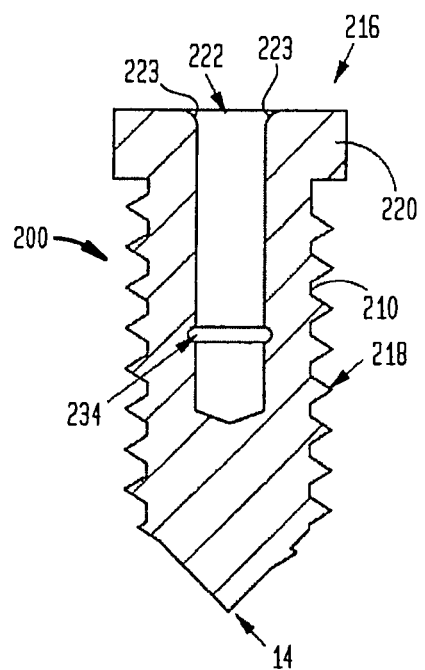
FIG. 19 shows a cross-sectional side view of an anchor main body forming a part of a second embodiment of a bone anchor device for anchoring a suture engaged with soft tissue to a bone in accordance with the invention.
Figure 20:
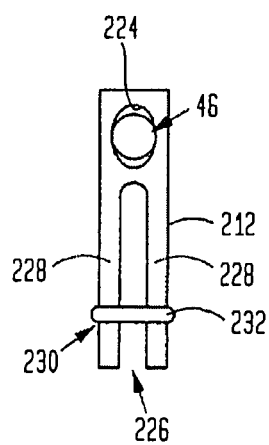
FIG. 20 shows a side view of an eyelet pin forming a part of the second embodiment of the bone anchor device for anchoring a suture engaged with soft tissue to a bone of which the anchor main body of FIG. 19 forms a part, the eyelet pin being configured to cooperate with the anchor main body of FIG. 19.
Figure 21:
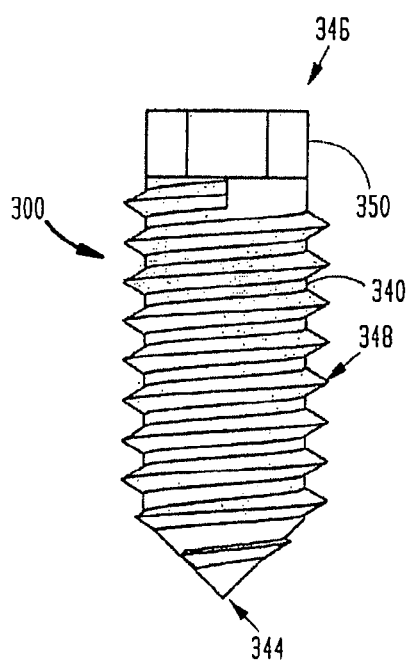
FIG. 21 shows a side view of an anchor main body forming a part of a third embodiment of a bone anchor device for anchoring a suture engaged with soft tissue to a bone in accordance with the invention.
Figure 23:
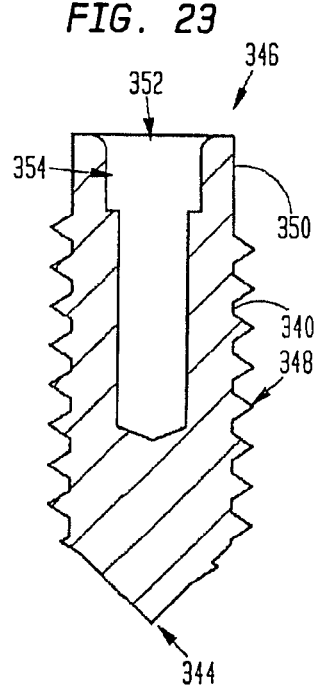
FIG. 23 shows a cross-sectional side view of the anchor main body of FIG. 21, along VII-VII of FIG. 22.
Figure 22:
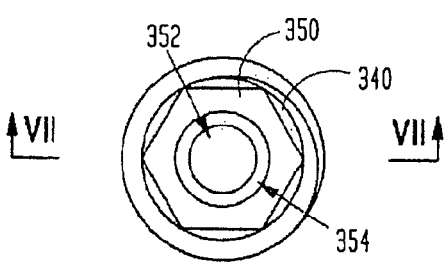
FIG. 22 shows a top view of the anchor main body of FIG. 21.

A second embodiment of the bone anchor device is shown in FIGS. 19 and 20. This bone anchor device is largely similar to the first embodiment shown in FIGS. 1-4, except for the manner and mechanism by which the eyelet pin engages the anchor body. Particularly, as in the above noted embodiments, both the anchor main body 210 and the eyelet pin 212 are formed of a metal material of a type already commonly used within the body of a person, e.g., a metal or metal alloy such as titanium, stainless steel and cobaltchrome alloys; a suitable polymeric material that is nonabsorbable such as polyethylene, poly-ether-ether-ketone (PEEK), poly-ether-aryl-ketone (PEAK); a resorbable polymer selected from homopolymers, copolymers and blends of polylactide, polyglycolide, polyparadioxanone, polytrimethylene carbonate or polycaprolactone; or composites of the aforementioned with biocompatible inorganic substances such as carbon, hydroxyapatite, beta tricalcium phosphate, other calcium phosphate ceramics or calcium sulfate.

The anchor main body 210 defines an operative leading end 214 and an operative trailing end 216 and a self-tapping thread 218 extending externally along the length thereof from its operative leading end towards its operative trailing end. At its trailing end 216 the body defines a head formation 220, the head formation being geometrically profiled to permit engagement with a screwdriver-type tool for screwing the body into a bone. The body 210 also defines a receiving formation 222 therein that is in the form of a cylindrical blind bore, the receiving formation 222 being particularly configured to securely receive an eyelet pin 212 therein.

The eyelet pin 212 defines a passage 224 therethrough near its proximal end and a longitudinal slot 226 that extends therein from the distal end. The pin thus defines two legs 228 on opposite sides of the slot 226. The pin 212 is configured to be securely locatable within the receiving formation 222 defined by the anchor main body 210, at least partially due to an effective friction fit, as in the first embodiment described above in connection with FIGS. 1-4. The inherent deformability of the material forming the pin 212 and the configuration of the slot 226 both serve to enhance the required location of the pin within the receiving formation 222 defined by the body 210. In order to further enhance the location of the pin 212 within the receiving formation 222 defined by the anchor main body 210, the pin 212 defines a peripheral groove 230 within which an elastic band, preferably an O-ring element 232, is received. The O-ring may, for instance, be made of silicone. The anchor main body 210 also defines a groove 234 within the receiving formation 222, the positioning of the grooves 230 and 234 being such that, with the pin inserted into its required operative configuration within the receiving formation 222 of the body 210, the grooves 230 and 234 will oppose one another, providing for the location of the O-ring element 232 therein, thus serving to further enhance the locking between the body and the pin when the pin is deployed downwardly into its closed position (hereinafter the "closed" position). It will be understood that the resilient elasticity of the O-ring element 232 and the slotted configuration of the pin 212 will permit the insertion of the pin 212 into the receiving formation 222 with the O-ring element effectively assembled into the groove 230, the O-ring element 232 again expanding when the grooves 230 and 234 oppose one another, as described above.

As in the first embodiment of FIGS. 1-4, with a suture 46 passing through the passage 224 and by the location of the pin 212 within the receiving formation 222 defined by the body 210, the segments of the suture extending from the section passing through the passage 224 are effectively gripped between the outer surface of the pin 212 and the inner surface of the passage 222 in the body 210, thus providing for effective anchoring of the suture, as will be explained in more detail hereafter. In order to prevent suture damage during the location of the pin 212 into the receiving formation 222 of the body 210, the end of the receiving formation 222 may be flared as shown at 223. The opposite ends of the passage 224 may be similarly flared. The formation of an effective cutting edge between the pin 212 and the body 210 is thus avoided, when the pin is inserted into the receiving formation 222 with a suture passing through the passage 224.

Third Set of Exemplary Embodiments

Figure 24:
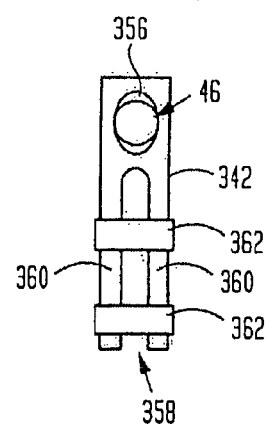
FIG. 24 shows a side view of an eyelet pin forming a part of the third embodiment of the bone anchor device for anchoring a suture engaged with soft tissue to a bone of which the anchor main body of FIG. 21 forms a part, the eyelet pin being configured to cooperate with the anchor main body of FIG. 21.

Referring now to FIGS. 21 to 25 of the drawings, a third embodiment of a bone anchor device 300 for anchoring a suture engaged with soft tissue to a bone in accordance with the invention includes a substantially cylindrical body 340 (shown in FIGS. 21-23) and an eyelet pin 342 (shown in FIG. 24). Both the anchor main body 340 and the eyelet pin 342 can be formed of materials equivalent to those referred to above. The anchor main body 340 again defines an operative leading (or distal) end 344 and an operative trailing (or proximal) end 346 and a self-tapping thread 348. At its trailing end 346, the body defines a geometrically profiled formation 50 that permits engagement with a screwdriver-type tool for screwing the body into a bone. For the purpose described hereafter, the effective diameter of the formation 350 is equal to or smaller than the diameter of the remainder of the anchor main body 340. The body 340 again defines a receiving formation 352 that is in the form of a cylindrical blind bore, the receiving formation 352, in this case, defining an enlarged trailing end segment 354, as illustrated. The receiving formation 352 provides for the secure location therein of the eyelet pin 342.

The eyelet pin 342 again defines a passage 356 therethrough near the proximal end thereof and a longitudinal slot 358 that extends therein from the distal end. The pin thus again defines two legs 360. The two legs, in this case, have bands 362 of a resiliently deformable material located thereon which, upon the location of the pin 342 in the receiving formation 352, enhance the secure location of the pin within the receiving formation.

Figure 25:
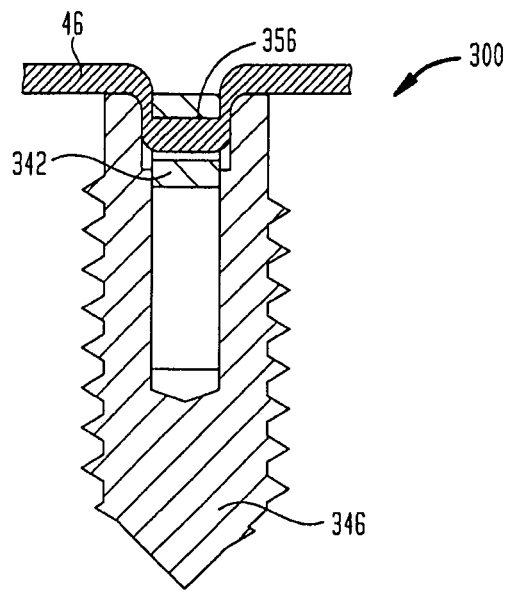
FIG. 25 shows a cross-sectional side view of an anchor main body and eyelet pin of a fourth embodiment of a medical device for anchoring a suture engaged with soft tissue to a bone in accordance with the invention, the pin being located in its closed configuration within a receiving formation defined by the anchor main body.

With a suture 46 passing through the passage 356 defined by the eyelet pin 342 and with the pin 342 fully inserted in the receiving formation 352 of the anchor main body 340, it will be appreciated that the suture 46 will take a tortuous path in the bone anchor device, as shown at 335 in FIG. 25, which shows the pin 342 disposed in the anchor body 342 in the closed position, particularly, insofar as the passage 356 will be located within the enlarged region 354 of the receiving formation 352.

Figure 26:
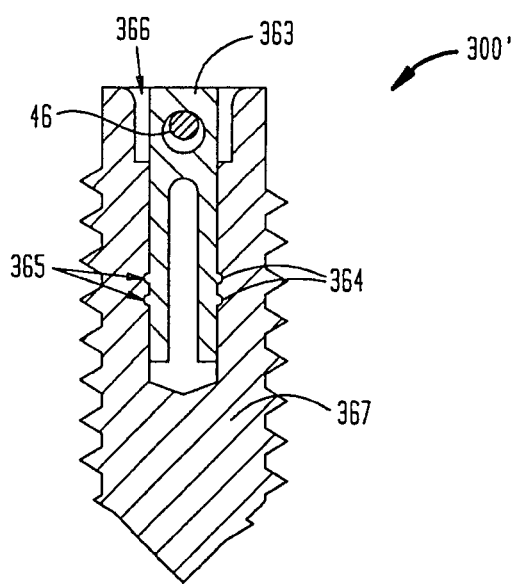
FIG. 26 shows the bone anchor device of FIGS. 19-24 in the closed state.

In relation to the bone anchor devices described above, it must be appreciated that their design may vary in different respects. By way of example and with reference to FIG. 26 of the drawings, an eyelet pin 363 of a bone anchor device 300' may define surrounding ridges 364 that are operatively located in complementary grooves 365 defined in the receiving formation 366 of the anchor main body 367 of the device, for the location of the pin in the receiving formation. This may be accommodated by the inherent resilient deformability of the material forming the pin 363. Clearly, the ridges may, alternatively, be defined within the receiving formation of the anchor main body 367 and complementary grooves may be defined within the eyelet pin 363. Any number of complementary formations may be defined for this purpose, whereas the exact configurations of these formations also are variable. Many other locating arrangements for this purpose also can be envisaged.

Fifth Set of Exemplary Surgical Procedures

The bone anchor devices 1, 200, 300, 300', described hereinabove may be used in connection with various different procedures that involve the anchoring of soft tissue to bone, which is required in relation to the repair of various different injuries, as described hereafter. This includes any of the surgical procedures described hereinabove such as those described in connection with FIGS. 8-12 and 13-15.

It will be understood that, in relation to the anchor main body 210, the head formation 220 in the second embodiment of FIGS. 19 and 20 will protrude from the bone with the anchor main body screwed into a bone, whereas, in relation to the anchor main body 340 in the third embodiment of FIGS. 21-25, the entire anchor main body can be screwed into a bone to become effectively embedded within the bone.

Figure 27:
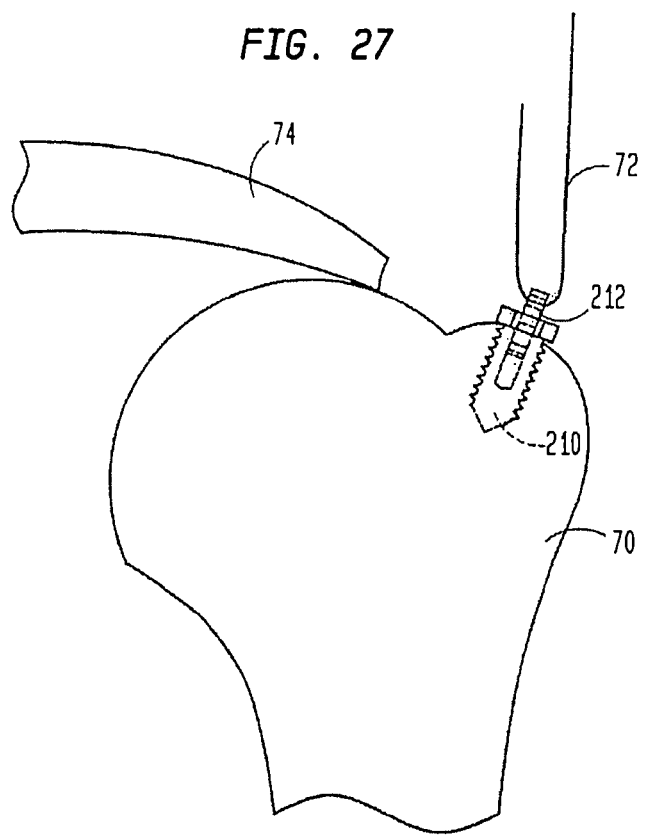
FIGS. 27 and 28 illustrate schematically a fifth procedure for attaching soft tissue to a bone and which includes the use of the second embodiment of the bone anchor device as illustrated in FIGS. 19 and 20.
Figure 28:
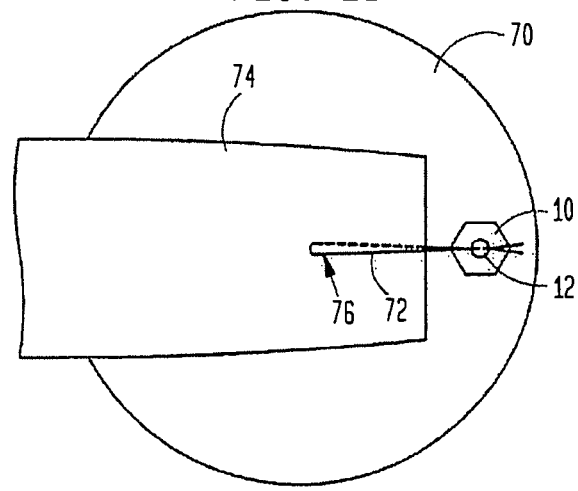

FIGS. 27 and 28 illustrate a fifth procedure or procedure step envisaged for performing a rotator cuff repair in accordance with the present invention and using the bone anchors of the present invention. FIGS. 27 and 28 illustrate this procedure utilizing the bone anchor 200 of the second embodiment illustrated in FIGS. 19 and 20 and provides for the anchor main body 210 to be screwed into the humerus 70 in a desired anchoring location. Prior to being screwed into the humerus, the anchor main body 210 has an eyelet pin 212 partially located therein, the eyelet pin 212 carrying a suture 72 as shown. It must be appreciated in this regard that the eyelet pin and suture also can be so placed immediately after the location of the anchor main body 210.

Following the location of the anchor main body 210 as shown and in order to provide for the required location of a damaged tendon 74 with respect to the humerus 70 with the aid of a suitable arthroscopic passing instrument, one end of the suture is passed through the tendon 74 and then again passed through the passage in the eyelet pin 212, thus in effect forming a closed loop 76, whereby the tendon is engaged. By thereafter applying tension to the two end segments of the suture 72, the tendon 74 is pulled towards the bone anchor device 200 into a required location with respect to the humerus 70 where re-attachment with the humerus is desired, following which the eyelet pin 212 is displaced into its closed configuration in which it is fully inserted into its receiving formation 222 defined by the anchor main body 210 to thereby effectively anchor the suture with respect to the bone anchor device 200. This position of the tendon 74 with respect to the humerus 70 is illustrated in FIG. 28, which also illustrates the loop 76 formed by the suture 72 which permits the tendon to be pulled into its required location as described. With the two ends of the suture 72 effectively gripped between the eyelet pin 212 and the anchor main body 210, required anchoring of the suture is achieved and the end segments of the suture 72 can then be cut off to provide the configuration shown in FIG. 28. It will be understood that, in relation to a particular tendon, two or more bone anchor devices 200 can be utilized, each bone anchor device being associated with the use of a suture as described. It must also be understood that, in relation to each bone anchor device used, two or more sutures may be passed through the passage of the eyelet pin thereof, wherein each suture can be passed through the associated tendon in the manner described.

It will be understood that essentially similar procedures can be performed except using the tissue fastener illustrated in FIGS. 5-7 to attach the suture to the tendon 74, rather than stitching through the tissue of the tendon.

Sixth Set of Exemplary Surgical Procedures

Figure 29:
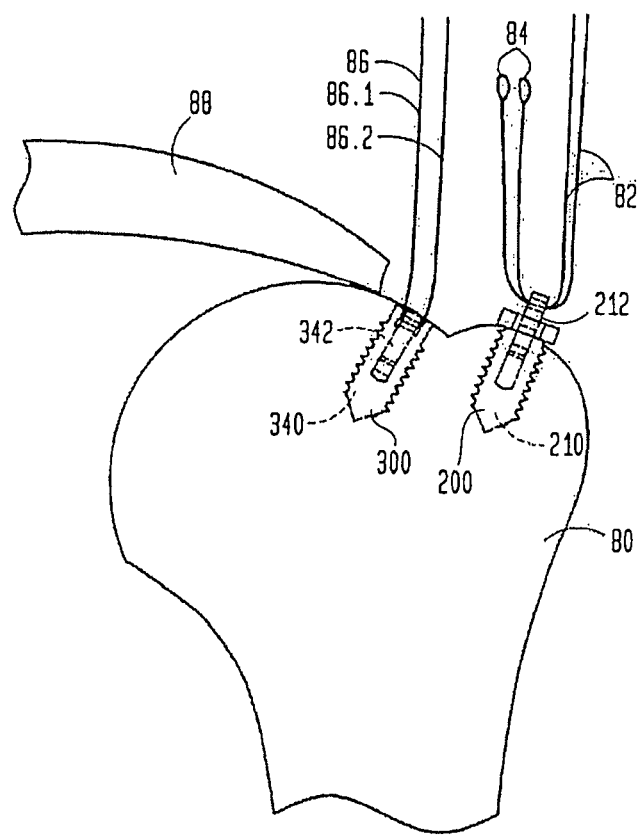
FIGS. 29 and 30 illustrate schematically a sixth procedure for attaching soft tissue to a bone and which includes the use of both the second embodiment of the medical device as illustrated in FIGS. 19 and 20 and the third embodiment of the medical device as illustrated in FIGS. 21 to 24.
Figure 30:
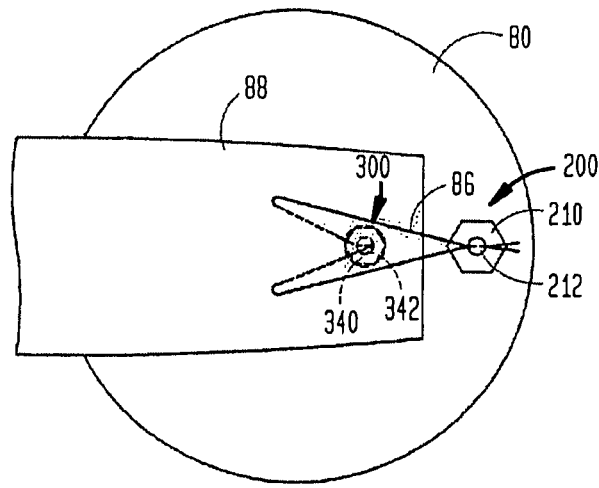

With reference to FIGS. 29 and 30 of the drawings, a sixth procedure or procedure step that is envisaged for performing a rotator cuff repair provides for an anchor main body 210 of a first bone anchor device 200 in accordance with the second embodiment as described in connection with FIGS. 19 and 20 and an anchor main body 340 of a second bone anchor device 300 in accordance with the third embodiment as described in FIGS. 21 to 24 to be screwed into the humerus 80 in locations as shown. The anchor main body 210 has an eyelet pin 212 partially located therein in the open position, the eyelet pin 212 having two separate sutures 82 passing through the passage defined by the eyelet pin 212, the sutures 82 defining loop formations 84 at one of their ends and serving as shuttling sutures as described hereafter.

The other anchor main body 340 has an eyelet pin 342 fully inserted therein, the eyelet pin 342 having a suture 86 passing through its passage. The suture 86 thus defines suture segments, 86.1 and 86.2 respectively that extend from the eyelet pin 342.

With the anchor main bodies 210 and 340 being located as shown, with the aid of a suitable passing instrument, each suture segment 86.1 and 86.2 is passed through the tendon 88 and then through a loop formation 84 in one of the shuttling sutures 82. Thereafter, by pulling on the ends of the shuttling sutures 82 remote from the loop formations 84, the shuttling sutures together with the suture segments 86.1 and 86.2, are pulled through the passage in the eyelet pin 212 of bone anchor 200, thus providing for each suture segment to form a loop that extends from the eyelet pin 342 of bone anchor 300 through the tendon 88 and back to the eyelet pin 212 of the bone anchor 200. Thereafter, by pulling on the suture segments 86.1 and 86.2, the tendon 88 is pulled towards its desired location with respect to the humerus 80 in which it should attach itself to the humerus 80, following which the eyelet pin 212 is displaced into its closed position, fully inserted in the receiving formation of the anchor main body 210. Thereby, the suture segments 86.1 and 86.2 are effectively anchored with respect to the bone anchor device 200. FIG. 30 particularly illustrates the operative configuration of the suture 86 with respect to the two bone anchor devices 200 and 300 used and a tendon 88 to be attached to the humerus 80. It must again be appreciated that further pairs of bone anchor devices 200, 300 can be utilized in a similar manner for the attachment of a tendon to a humerus, thus providing a more effective attachment footprint that will ensure the effective attachment of a tendon to a humerus.

In alternate embodiments, this surgical technique can be practiced with medial bone anchors of other designs, including conventional designs, than the bone anchor 300 of the present invention.

Seventh Set of Exemplary Surgical Procedures

Figure 31:
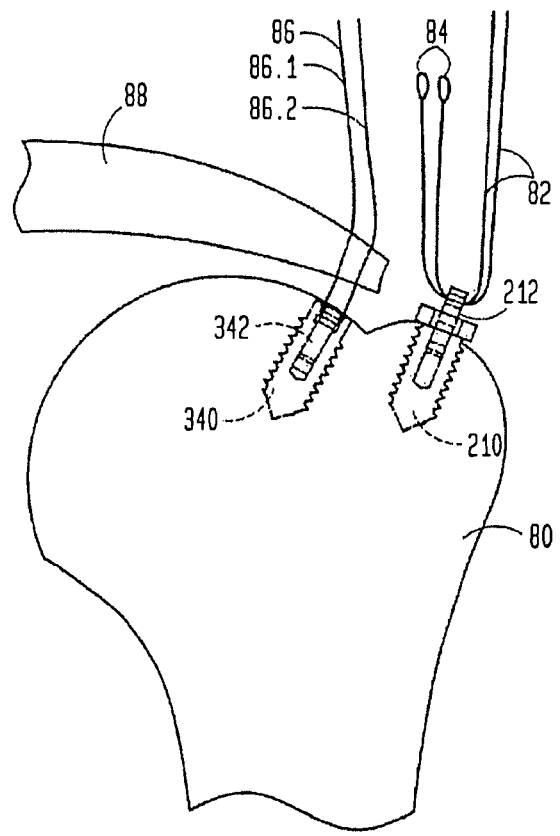
FIGS. 31 and 32 illustrate a variation of the procedure illustrated in FIGS. 29 and 30 in accordance with the invention.
Figure 32:
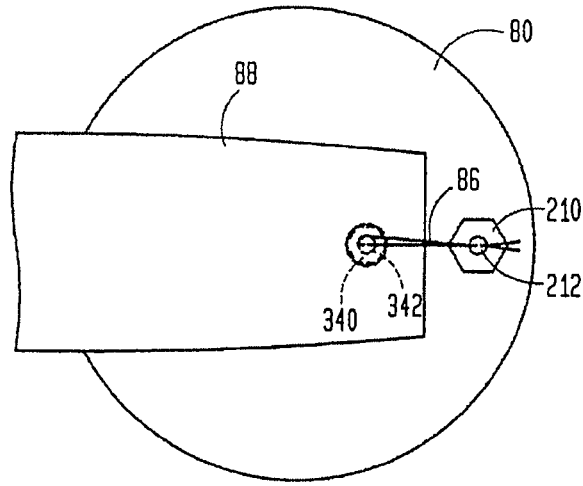

As a variation of the above sixth procedure, and as illustrated in FIGS. 31 and 32, for the location of the anchor main body 340 in the humerus, it is first displaced through the tendon 88 and then screwed into the humerus 80 in the location shown. By doing so the two segments 86.1 and 86.2 of the suture 86 are effectively passed through the tendon 88, as illustrated in FIG. 31. The remainder of the procedure is effectively the same as before, thus providing the anchored suture configuration as shown in FIG. 32.

Eighth Set of Exemplary Surgical Procedures

Figure 33:
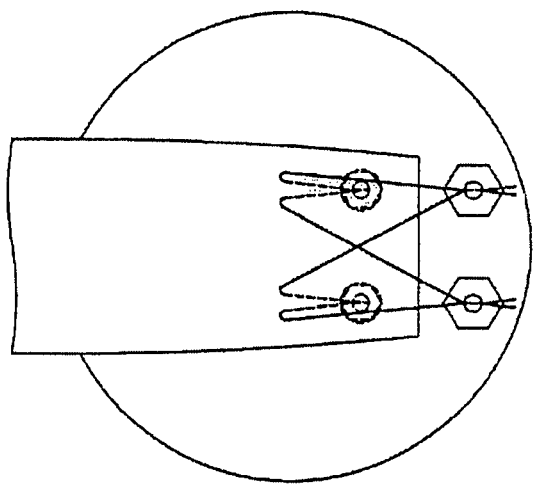
FIGS. 33 to 35 illustrate three further procedures for attaching soft tissue to a bone and which include the use of bone anchor device in accordance with the invention.
Figure 34:
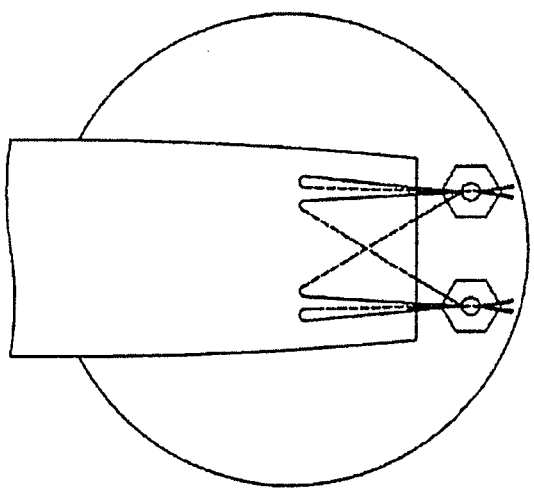
Figure 35:
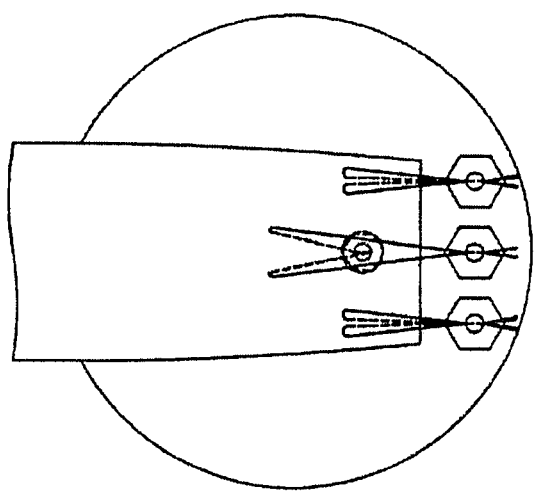

FIGS. 33 to 35 illustrate still further repair procedures in relation to the use of bone anchor devices as above described, FIG. 33 illustrating a procedure similar to that illustrated in FIGS. 29 and 30 except insofar as two pairs of bone anchor devices are used and one suture segment of the respective sutures crosses over as illustrated, in order to again create a more effective attachment footprint to provide for the secure attachment of a tendon to a humerus.

FIG. 34 also illustrates a cross-over procedure as above envisaged, but in relation to the procedure as illustrated in FIGS. 27 and 28, whereas FIG. 35 illustrates a procedure that involves a combination of the procedures described in FIGS. 27 and 28 and in FIGS. 29 and 30, as is clearly apparent. FIG. 35 illustrates a dual row fixation method, it being submitted that, in association with the repair of rotator cuff injuries, depending on the nature of individual injuries, particularly suitable repair procedures can be utilized in order to enhance and render most effective the repair of injuries. It will be appreciated that many further variations within the above procedures can be envisaged, a major benefit of the use of the procedures being that the need for suture knotting is completely eliminated, which will, in turn, significantly facilitate general suture management.

Fourth Set of Exemplary Embodiments

Figure 36:
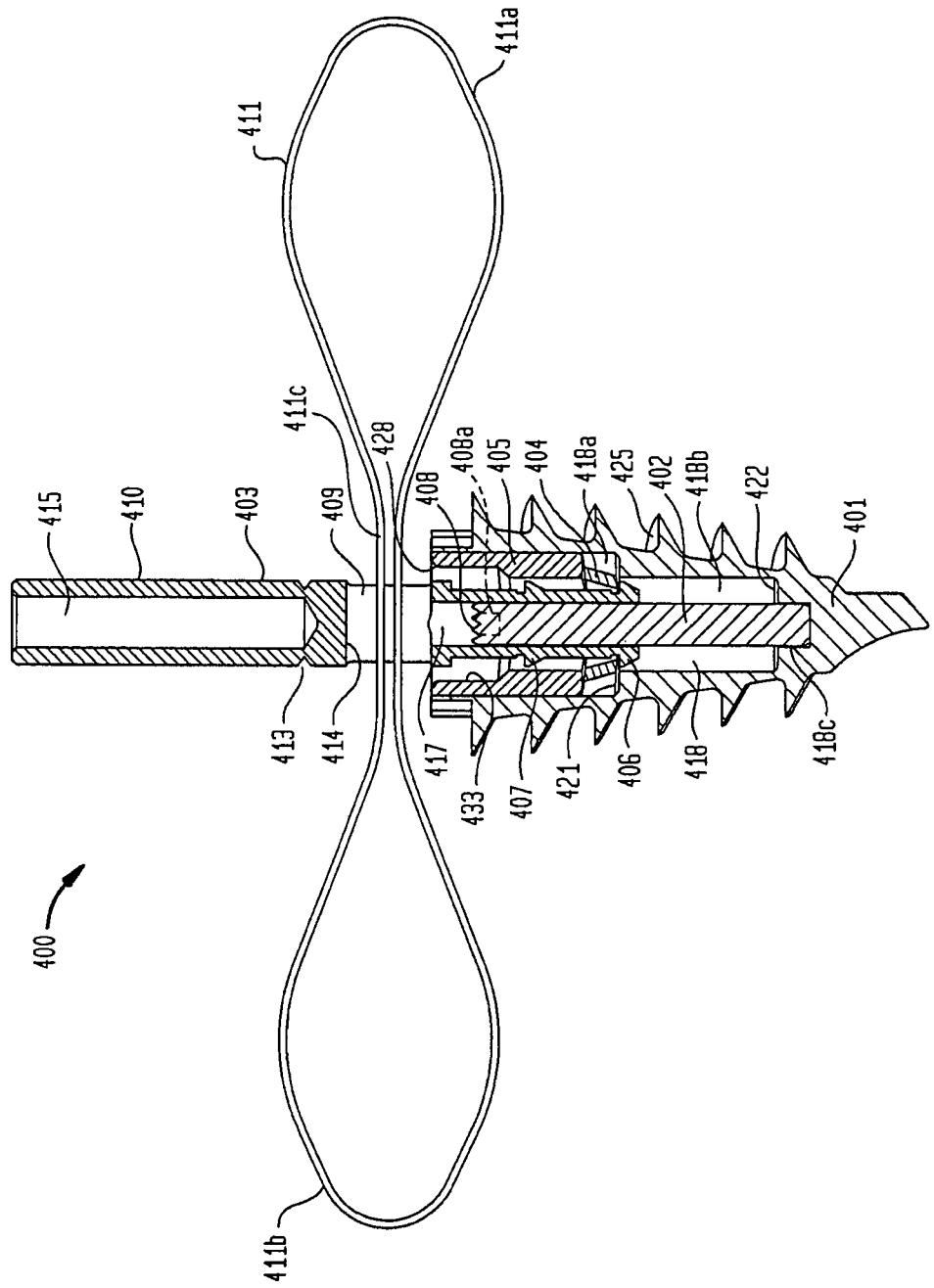
FIG. 36 shows a cross-sectional side view of a bone anchor device in the open state in accordance with a third embodiment of the invention for anchoring a suture engaged with the soft tissue to a bone.
Figure 37:
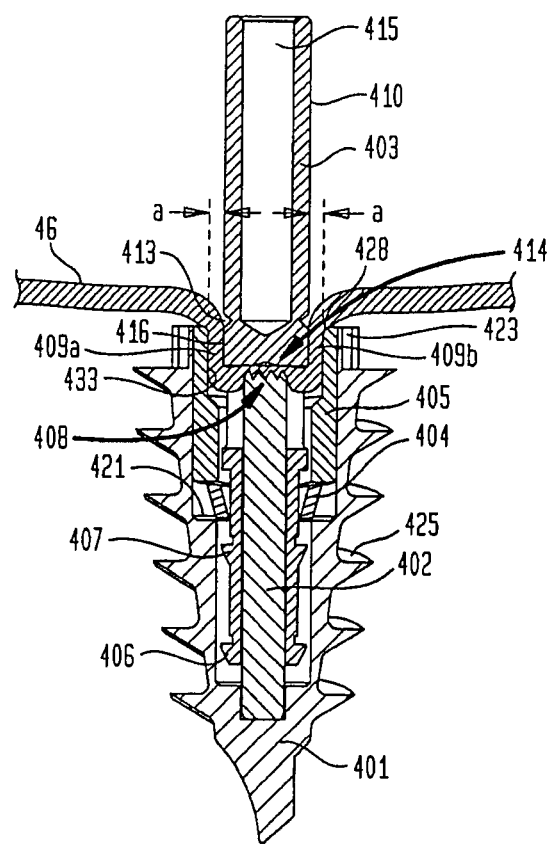
FIG. 37 shows a cross-sectional side view of the bone anchor device of FIG. 36 in the closed state.
Figure 38:
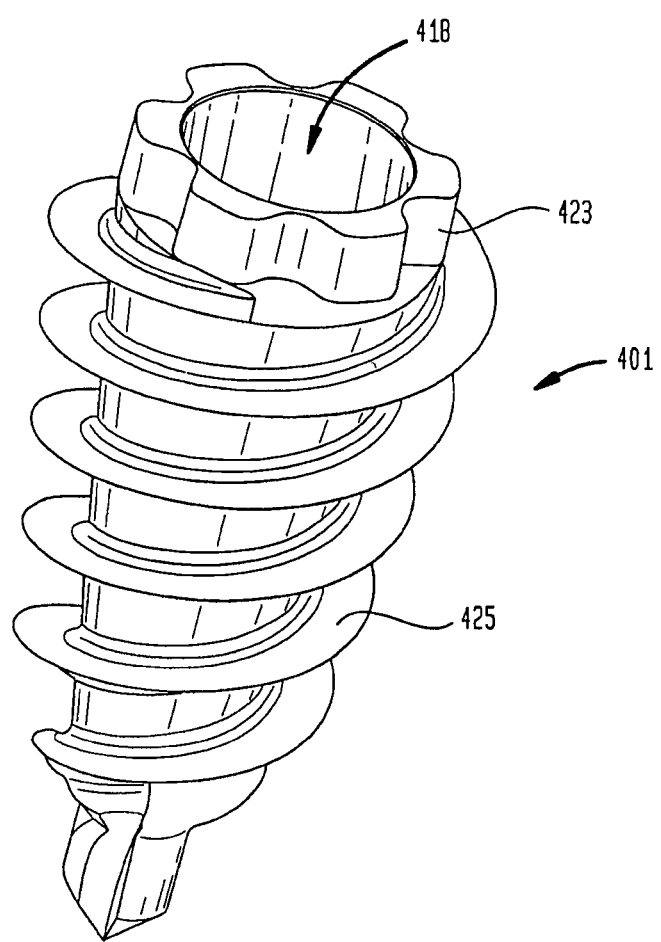
FIG. 38 shows a perspective view of the anchor main body portion of the bone anchor device of FIG. 36.
Figure 39:
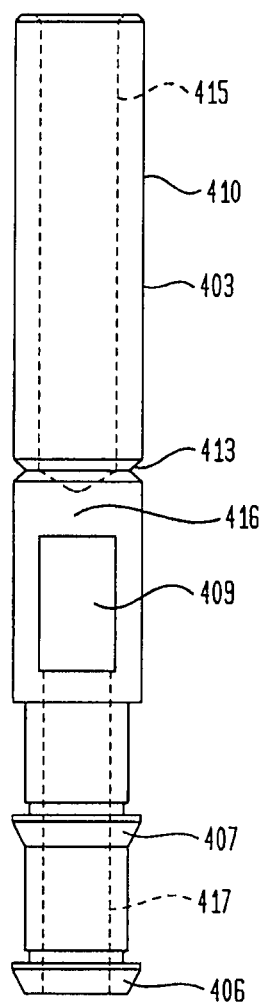
FIG. 39 shows a side view of the eyelet pin of the bone anchor device of FIG. 36.
Figure 40:
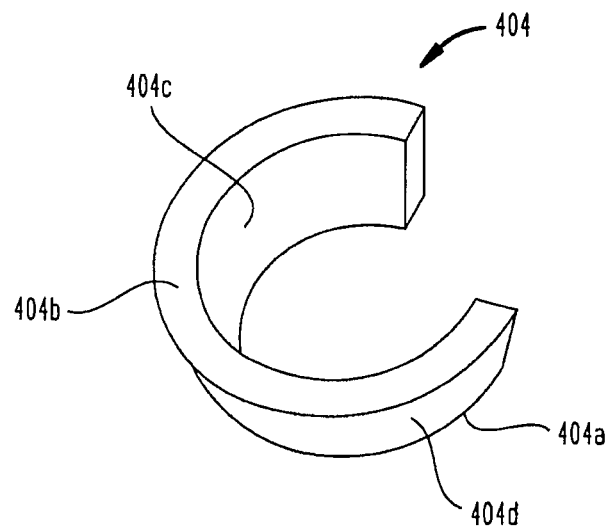
FIG. 40 shows a perspective view of a C-ring that can be employed as the locking ring of the bone anchor device of FIG. 36.
Figure 41:
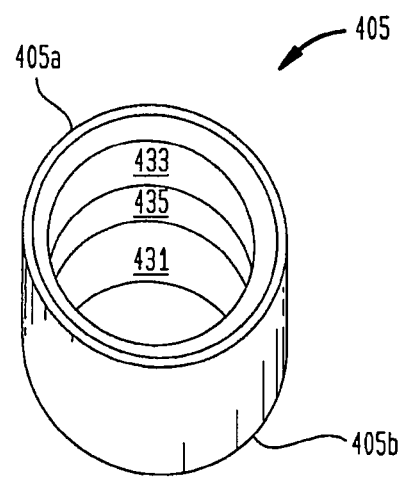
FIG. 41 shows a perspective view of the retainer of the bone anchor device of FIG. 36.

FIG. 36 is a cross-sectional side view of a bone anchor device 400 in the open state in accordance with a fourth embodiment of the present invention. FIG. 37 is a similar cross-sectional view, except showing the device 400 in the closed state. FIGS. 38-42 show some of the components of the overall bone anchor device 400 individually (i.e., disembodied from the overall device 400) for greater clarity.

Bone anchor device 400 in accordance with the fourth embodiment comprises a threaded anchor main body 401 (shown disembodied from the device in FIG. 38) in the nature of a screw or awl bearing threads 425, which can be screwed into a bone in a desired location as previously described. The anchor main body 401 comprises a central longitudinal bore 418 that is open at the proximal end and closed at the distal (or tip) end. The bore 418 comprises three segments, i.e., 418a at the proximal end, 418b in the intermediate portion, and 418c at the distal end. Segment 418a has the largest internal diameter, section 418b has an intermediate diameter, and segment 418c has the smallest diameter. The interface between segments 418a and 418b defines a first shoulder 421 and the interface between segments 418b and 418c defines a second shoulder 422. A shaped head 423 is provided at the proximal end of anchor main body 401 for engagement by a driving device such as a screwdriver or other geometrical driver, such as a Torx arrangement.

In other embodiments of this (or any of the other anchor main bodies described herein), the threads 425 on the anchor main body may be eliminated or reduced in size or replaced with ridges, striations, or other external formations and the bone anchor can be inserted into the bone by pounding (as in the nature of nail), instead of screwing. In such embodiments, a hole may be pre-drilled into which the anchor main body 401 is inserted.

A central pin 402 extends longitudinally in bore 418. The central pin 402 has a diameter slightly smaller than the diameter of distal bore segment 418c of anchor main body 401 such that it fits within segment 418c snugly but freely slidably therein in the longitudinal direction and freely rotatable about its longitudinal axis. In a preferred embodiment of the invention, the bore 418 and the pin 402 are cylindrical so that the pin 402 can rotate about its longitudinal axis relative to the anchor main body, which is a useful feature in many applications, as will be discussed in more detail below. However, in other embodiments, they may have non-cylindrical profiles since it is not required that the elements be rotatable relative to each other.

The proximal end 408 of the central pin 402 may be textured as shown to help grip sutures as will be discussed in more detail herein below. The texturing may take any number of forms. In one embodiment as illustrated, it comprises a series of peaks and valleys in the nature of an egg carton type shape. However, in other embodiments, the texturing may comprise parallel ridges, corrugations, serrations, divots, or general roughening of the surface. In yet another embodiment, a bore as shown in phantom at 408a in FIG. 36 may be formed in the central pin 402a.

Next, an eyelet pin 403 (shown separately in FIG. 39) is disposed in the longitudinal bore 418 of the anchor main body 401 over the central pin 402. Particularly, eyelet pin 403 includes a transverse eyelet 409 intermediate its proximal and distal ends. One or more sutures will pass through the eyelet 409 and be locked in the device during the surgical procedure, as will be described in more detail herein below. Eyelet pin 403 includes a proximal bore 415 proximal of the eyelet 409 and a distal bore 417 distal of the eyelet 409. In the particular embodiment illustrated in FIGS. 36, 37, and 39, the proximal bore is blind to the eyelet 409, i.e., eyelet 409 and proximal bore 415 are not in communication with each other. However, as will be discussed below, in alternate embodiments, proximal bore 415 may extend completely through to and into communication with eyelet 409, e.g., as illustrated in FIG. 44F, discussed further below. The proximal longitudinal bore 415 is for the purpose of accepting a longitudinal member of an impactor tool as will be described in further detail herein below.

Distal bore 417 is open to and in communication with the eyelet 409. The diameter of distal bore 417 is equal to or slightly smaller than the diameter of central pin 402 so as to form an interference fit with the central pin, as will be described in more detail herein below. Thus, when assembled (in either the open position shown in FIG. 36 and the closed position shown in FIG. 37), the eyelet pin 403 and central pin 402 are not rotatable relative to each other, but the assembly of the eyelet pin and central pin collectively is freely rotatable relative to the anchor body because the central pin is freely rotatable in bore 418.

The distal portion of eyelet pin 403 includes two ramp formations 406 (near the distal end) and 407 (intermediate the distal end and the eyelet 409).

The proximal portion of the eyelet pin is a breakaway portion that will be removed from the body prior to the end of the surgery. The breakaway portion 410 is defined by a weakened section that can be broken relatively easily. This may be provided by a thinning of the material of the eyelet pin, such as by fabricating a radial notch or V-groove in the material, as illustrated at 413 in FIGS. 36 and 37.

The eyelet extension portion 410 serves several important functions. For instance, essentially the rest of the bone anchor device 400 other than extension 410 is embedded in and below the bone surface after installation of the bone anchor device in bone and, thus, is extremely difficult for the surgeon to see once installed, particularly in an arthroscopic procedure. However, the breakaway portion 410 of eyelet pin 403 protrudes substantially from the bone and is, therefore, easy to visualize. In one embodiment, at least the extension portion 410 of the eyelet pin 403 is brightly colored to even further enhance its visibility.

A locking ring helps retain the eyelet pin 403 in the anchor main body. In the embodiment shown in FIGS. 36 and 37, the locking ring 404 is a C-shaped ring (also shown separately in FIG. 40).

Locking ring 404 is made of a strong resilient material such as a metal or polymer so that, upon application of sufficient force in the radial direction, it can be spread radially outwardly, or squeezed radially inwardly, to change its diameter and return elastically when the force in the radial direction is removed. The inner and outer surfaces 404c, 404d of locking ring 404 are conical rather than cylindrical is shape. That is, inner and outer surfaces 404c, 404d are not parallel to the longitudinal axis 405 of locking ring 404 (i.e., up-down in FIGS. 26 and 37). Thus, a force applied to either surface 404c or 404d in the longitudinal direction (such as by ramp formations 406 or 407 on eyelet pin 403 hitting the inner surface 404c of locking ring 404 as eyelet pin 403 travels longitudinally in bore 418 of anchor main body 401) will be converted partially to force in the radial direction. Thus, if either ramp formation 406 or 407 meets the inner surface 404c of locking ring 404 with sufficient force, it can cause locking ring to radially expand outwardly, permitting that ramp formation to pass through the locking ring 404. When the force is removed, locking ring 404 returns elastically to its stress free (or unbiased) state.

Locking ring 404 is designed such that the required amount of force to make that happen is greater than could normally be applied accidentally, but that will permit ramp formations 406 and 407 to pass through locking ring by a moderate strike with a mallet on the proximal end of eyelet pin 404 during assembly or during surgery such, as will be described in further detail herein below.

An insert 405 is disposed in the proximal segment 418a of axial bore 418 in the anchor main body 401, as seen in FIGS. 36 and 37. The insert 405 also is shown separately in FIG. 41. Insert 405 is essentially a hollow cylinder having a constant outer diameter equal to or slightly larger than the inner diameter of proximal segment 418a or bore 418 in anchor main body 401, but comprising two sections 431 and 433 of different internal diameter. The distal section 431 has a narrower inner diameter than the proximal segment 433, thereby forming a shoulder 435 therebetween. Accordingly, insert 405 forms an interference fit within bore segment 418a essentially permanently fixing it in bore segment 418a in the position shown in FIGS. 36 and 37.

The inner diameter of the distal segment 431 of insert 405 is smaller than the largest external diameter of locking ring 404. The inner diameter of intermediate segment 418b of bore 418 in anchor main body 401 is smaller than the smallest outer diameter of locking ring 404. Accordingly, locking ring 404 is captured in segment 418a of bore 418 of anchor main body 401 between shoulder 421 between bore segments 418a and 418b and the distal end 405b of insert 405. The longitudinal length of insert 405 is selected so that, when insert 405 is fully inserted in bore 418 with its proximal end 405a essentially flush with the proximal end of anchor main body 401, the distance between the distal end 405b of insert 405 and shoulder 421 in axial bore 418 is slightly greater than the height of locking ring 404, thus essentially capturing locking ring 404 in the position as shown in FIGS. 36 and 37.

The bone anchor device 400 is assembled by first inserting the central pin 402 into bore 418 in the anchor main body 401. Particularly, it is inserted into the distal bore segment 418c of the anchor main body 401, as previously mentioned. Next, locking ring 404 is inserted into bore 418 where it will sit on shoulder 421. Next, insert 405 is press fit into proximal section 418a of bore 418, as previously described to capture locking ring 404 between insert 405 and shoulder 421.

Then, eyelet pin 403 is inserted into bore 418. Specifically, eyelet pin 403 falls readily through proximal bore segment 418a until it reaches central pin 402. whereupon it must be forced further downward over central pin 402 into an interference fit between the central pin 402 and the distal bore 415 of the eyelet pin 403, In addition, sometime after central pin 402 is in distal bore 415, ramp formation 406 comes into contact with the inner surface 404c of locking ring 404. Particularly, the largest diameter of ramp formation 406 is larger than the smallest diameter of the inner surface 404c of locking ring 404 when locking ring 404 is in its unbiased condition. Only upon application of significant downward force applied to ramp 406 on locking ring 404 will locking ring 403 be forced to expand radially sufficiently to permit ramp 406 to pass through.

Accordingly, sufficient force is applied downwardly on eyelet pin 403 to permit ramp formation 406 to pass through locking ring 404 (while simultaneously overcoming the continuing resistance to longitudinal movement of the eyelet pin 403 relative to the central pin 402 due to the aforementioned interference fit between the central pin 402 and the distal bore 415 of the eyelet pin 403. Once ramp 406 is through, the force is relieved and locking ring 404 returns to its stress-free state. At this point, the eyelet pin is now constrained in anchor main body 401 in the open position by virtue of first ramp formation 406 preventing the, now joined, eyelet pin 403 and central pin 402 from being pulled out proximally and the interference fit between central pin 402 and eyelet pin 403 preventing the joined eyelet pin 403 and central pin 402 from being pushed further into the bore 418 than the point at which the distal end of center pin 402 bottoms out in bore portion 418c. Accordingly, eyelet pin is axially trapped in anchor main body 401 with no or a very limited range of axial movement.

Only when sufficient downward force is again applied to eyelet pin 403 to (1) overcome the resistance to relative axial movement between the center pin 402 and the eyelet pin 403 resulting from the interference fit and (2) cause ramp formation 407 to expand locking ring sufficiently for ramp 407 to pass through locking ring 404 can eyelet pin 403 be disposed into the closed position as shown in FIG. 37.

Figure 49:
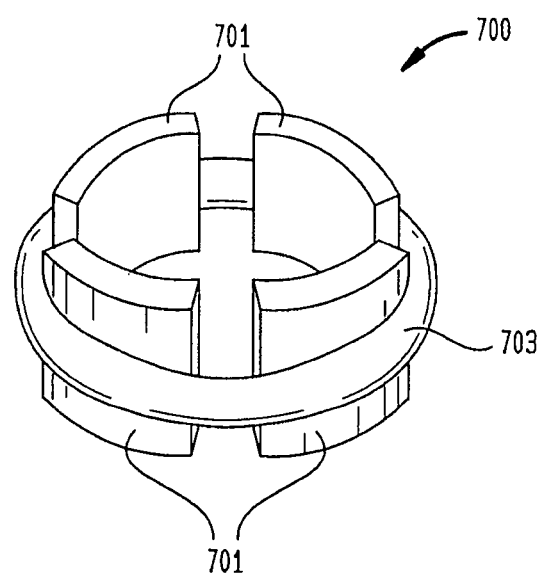
FIG. 49 shows a perspective view of an alternate locking ring to that illustrated in FIG. 40.

The locking ring 404 illustrated in the Figures is exemplary. Other devices, particularly, other elastically deformable rings, can be substituted for the locking ring, such as an elastically deformable closed ring or a split ring (neither shown in the Figures). FIG. 49, for example, illustrates another ring structure 700 comprising four crescent elements 701 having grooves within which an O-ring 703 can be inserted into in a radial constraining arrangement. This arrangement 700 will operate essentially in the same manner as the above-described locking ring.

Exemplary Embodiments of a Driving Tool

Figure 45:
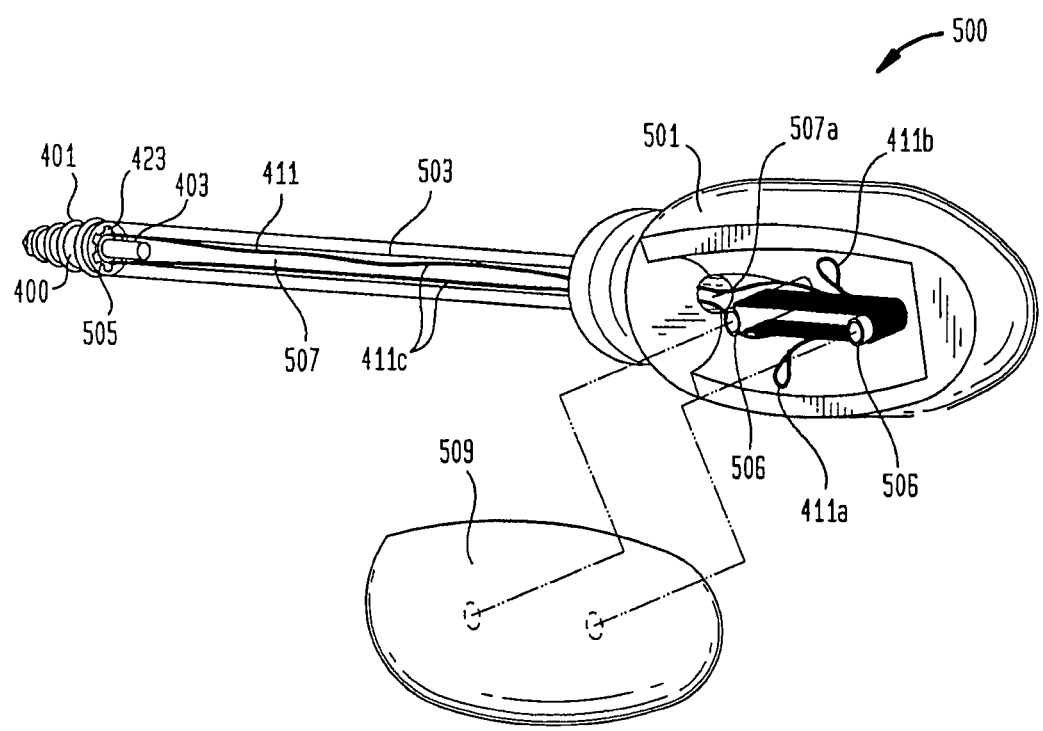
FIG. 45 is a semi-transparent perspective view of a driver for driving a bone anchor device into bone in accordance with an embodiment of the present invention.

FIG. 45 shows a perspective view of an exemplary bone anchor driver tool 500. It comprises a cannula 503 defining an internal bore 507 and a handle 501 coupled to the proximal end of the cannula, with the proximal end 507a of the bore 507 being open to and in communication with the hollow interior of the handle 501.

As will be described in further detail immediately below, the ends of a suture shuttling mechanism, such as a wire or suture loop 411 or a long suture with a loop at each end threaded through the eyelet pf the eyelet pin of a bone anchor device of the present invention, may run up the cannula 503 of the driver tool and extend into the hollow handle. The ends of the suture shuttling wire (or suture) may be wrapped around two pins 506 inside of the handle 503 for stowage and safe keeping prior to and during surgery. The handle can include a cap 509 to close off the handle if desired for better containment of sutures or suture shuttling mechanism 411, as will be described in detail further below. The bore is also open at recess 507b to the distal end of the cannula 507. The recess 507b at the distal end of the cannula is matingly shaped to engage the shaped head 423 of the anchor main body 401 of the bone anchor device so as to impart rotation to the anchor main body 401. As shown, when the driver 500 is engaged with the head of the anchor main body 401 of the assembled bone anchor device 400, the proximal end of the eyelet pin 403 extends within the cannula 507 of the driver 500. Preferably, the recess 507b is fashioned with gripping means, such as a slight interference fit over part of the mating surfaces of head 423 and recess 507b, so as to temporarily grip the head 423 of the anchor main body and hold it firmly so that the bone anchor device will not fall out of the driver unintentionally, but which can be released with moderate force once bone anchor 400 has been surgically located.

Ninth Set of Exemplary Surgical Procedures

The bone anchor device of FIGS. 36-41 can be used in surgical procedures for attaching soft tissue to bone such as those described herein above in connection with FIGS. 8-12, 13-15, and 16.

In fact, the various bone anchor and tissue fastener devices disclosed herein may be used in any number of surgical procedures, including those specifically described herein. In some such procedures, it may be desirable to provide a suture shuttle mechanism directly associated with the bone anchor device for shuttling sutures from the tissue fastener device or tissue (if no tissue fastener device is used) to the bone anchor device and, particularly, through the eyelet 409. In accordance with such embodiments, a shuttling mechanism comprising a flexible elongated member such as aforementioned wire loop 411 may be provided as shown in FIG. 36 passing through the eyelet 409. Wire loop 411 may be considered to comprise three segments, namely, opposing curved ends 411a and 411b, which are joined by linear segment 411c. Sutures may be inserted through one end of the loop, such as end 411b by a suitable instrument. The other end of the loop 411a may be pulled on to draw the loop 411, along with the shuttled sutures, through the eyelet 409. For instance, in one particular embodiment, the bone anchor device 400 is delivered to the surgeon already mounted on the driver tool 500. The loop 411 is long enough so that, with the center of the loop passing through the eyelet 409 of the eyelet pin 403 of the bone anchor device, both ends of the loop can extend up the entire length of the cannula 507 of the driver tool 500 and extending from the proximal end 507a of the cannula 507 into the handle 501, as shown in FIG. 45 illustrating the exemplary driver tool 500. Initially, the ends of the loop 411 may be wrapped around the two pins 506 for safe keeping within the interior of the handle. At the appropriate point in the surgical procedure, the wire ends can be unwrapped from the pins 506 so that both ends can be removed from inside the handle 503 of the tool 500 and may be manipulated manually by the surgeon externally of the patient. Having both ends of the loop extending from the driver tool provides several advantages. First, it can be used to shuttle sutures through the eyelet in either direction. Second, it helps prevent accidental deployment of one or both ends of the loop out of the instrument 500 and into the deployed position illustrated in FIG. 36. Particularly, if one or both ends of the loop 411 are disposed near the bottom of the tool 500, then a slight withdrawal of the tool from the bone anchor could release the end of the loop from the cannula. With both ends of the loop extending from the proximal end of the tool 500, this is much less likely. In addition, the surgeon can manually hold on to both ends, 411a and 411b, of the loop 411 in order to prevent one or both ends from being pulled through accidentally.

In any event, in an exemplary procedure, the surgeon would pull on one end of the loop, e.g., end 411a, until the other end 411b is released from the distal recess 507b of the cannula 507 of the tool 500 and into the deployed state. Then, the surgeon would thread the suture(s) to be shuttled through the eyelet 409 of the bone anchor device through the deployed end 411b. After the sutures have been threaded through end 411b, the surgeon would merely need to grasp end 411a with his hand and pull so as to pull end 411b through the eyelet 409 and up through the cannula 507 until the end 411b of the loop 411 comes completely through the cannula 507, carrying the suture(s) with it. The surgeon can then disengage the suture(s) from the loop and manipulate the suture(s) directly, e.g., so as to pull the required tension on them before locking the eyelet in the closed position and cutting the free ends of the sutures.

The shuttling mechanism 411 may be made of thin, flexible wire. However, in alternate embodiments, it may be fabricated of any string or filament and, in fact, may be formed of suture itself. In an even further embodiment of the invention, the suture shuttle 411 need not be a closed loop. For example, the shuttling mechanism might be comprised of a length of suture folded in half, wherein the fold at the midpoint of the suture comprises the distal end 411b of the shuttling mechanism 411 and the two ends of the suture comprise the proximal end of the suture shuttle. To assist with shuttling, small loops may be formed in the ends of the suture (or other filament), such as illustrated by the suture shuttle shown in FIG. 45.

The bone anchor device 400, including the anchor main body 401, the central pin 402, the eyelet pin 403, the locking ring 404, and the insert 405, is delivered to the surgeon in the assembled, open state as shown in FIG. 36. During surgery, the surgeon will install the device 400 in bone by screwing it into a bone using a suitable driving device engaged with the head 423, such as driver tool 500 described herein above in connection with FIG. 45. Note that one of the beneficial features of the present invention is that, since the eyelet pin/central pin assembly is freely rotatable inside the anchor main body, there is relatively less need to worry about the rotational alignment of the anchor main body 401 when it is being screwed into the bone as compared to conventional suture anchors where the eyelet orientation is fixed. It can be screwed in to any rotational position because the eyelet pin 403 is freely rotatable therein to align the eyelet 409 to face in the desired direction (i.e., in the direction from which the sutures will enter the device 400).

Once installed, the surgeon will shuttle sutures through the eyelet of 409 in the eyelet pin 403 either using a shuttling mechanism such as the wire shuttling device 411 or another device so that one or more sutures pass through eyelet 409. Then, the surgeon will place an impactor tool into the proximal bore 415 in the extension portion 410 of eyelet pin 403. In an arthroscopic procedure, this would be done through a cannula. Then, while the surgeon is tensioning sutures acting on the tissue to locate the tissue in an appropriate anatomical position, sufficient force would be applied to the proximal end of the impactor tool, such as by hitting it with a mallet or using it in conjunction with a spring-loaded or pneumatic impacting device to pound the eyelet pin 403 with sufficient force to cause the second ramp formation 407 to spread apart locking ring 404 allowing it to pass through so that the eyelet pin 403 slides down over the central pin 402 into the closed position as shown in FIG. 37. Particularly, after ramp 407 passes locking ring 404, the interference fit between eyelet pin 403 and central pin 402 lock the two pieces 402, 403 together in the closed position.

As the eyelet pin 403 is driven down into the closed position, the suture(s) 46 passing through the eyelet at 409 gets trapped in at least one of three locations. First, as seen in FIG. 37, suture(s) may be crushed between the roof 414 of the eyelet 409 and the proximal end 408 of the central pin 402. Surgical sutures are highly compressible and deformable without breakage and the design of the interface between proximal end 408 of central pin 402 and roof 414 of the eyelet 409 accommodates varying suture diameters and numbers of sutures. Therefore, the length of central pin 402 should be selected relative to eyelet pin 403 so that the spacing between the roof 414 of eyelet 409 and the proximal end 408 of central pin 402, when in the closed position, is between zero and a full suture diameter, and preferably between about ⅛ and ¼ of a suture diameter wherein the locked, closed position. The features (e.g., roughening, peaks and valleys, serrations) at the proximal end 408 of the central pin 402 help better grip the sutures.

In addition, depending on the diameter of the central pin 402 relative to the cross section of the eyelet pin (i.e., the area in the direction transverse to the direction of the passage through the eyelet between its ends 409a and 409b), it is possible for sutures to become trapped between the radial circumferential surface of the central pin 402 and the side walls of the eyelet. These locations for trapping sutures 46 can be seen, for instance, in FIG. 44B, which will be discussed further below. Particularly, if the diameter of the central pin is smaller than the cross section of the eyelet 409 by less than the thickness of two sutures (and is centrally located in the eyelet in the direction transverse the passage and perpendicular to the longitudinal axis, i.e., in and out of the page in FIG. 37 or left and right in FIG. 44B), any sutures that do not become trapped between the proximal end 408 of the central pin 402 and the roof 414 of the eyelet 409 will be compressed and therefore, securely held between the side of the central pin and the side walls of the eyelet.

In addition, the suture(s) take on a tortuous shape, such as the W shaped illustrated in FIG. 37, thus providing even greater resistance to being pulled free of the bone anchor device 400.

In one embodiment of the invention, the features are small enough and deep enough so that they individually bore into the suture and split the fibers of the suture to provide an even stronger grip.

In addition, the suture is crushed between the surface 416 of eyelet pin 403 and the surface of the inner surface of the distal segment 433 of insert 405 at the transverse ends 409a, 409b of the eyelet 409. Specifically, the outer surface 416 of the eyelet pin 403 just above the eyelet 409 has a diameter relative to the inner diameter of the proximal segment 433 of insert 405 such that the clearance between the two surfaces is less than the width of the suture. The clearance preferably also may be somewhere between zero and ½ of the diameter of the suture, and more preferably somewhere between ⅛ and ¼ the diameter of the suture.

Note that the eyelet 409 need not even be completely within the receiving formation for there to be significant capturing of the suture. Specifically, even if the eyelet is only partially within the receiving formation in the longitudinal direction when in the closed position, the suture will be compressed between the roof 414 of the eyelet pin and the proximal end of the main anchor body as long as the distance (or clearance) between the roof 414 of the eyelet pin and the proximal end of the main anchor body in the longitudinal direction is less than a width of a suture (and those two surfaces are not too far from each other in the radial (or transverse) direction.

In alternate embodiments, the central pin 402 need not compress the suture against the roof of the eyelet at all, there being sufficient crushing and fixing of the suture in the other two locations in the lateral space between the inner diameter of the proximal portion 433 of the insert 405 and the surface 416 of eyelet pin 403.

In yet other embodiments, the roof 414 of the eyelet pin 403 may also be configured to help grip the suture. For instance, it may be provided with mating features to the features on the proximal end 408 of the central pin 402. Alternately, the roof 414 may have different features, such as roughening, serrations, corrugations, ridges, etc. In even further embodiments, the proximal end 408 of the central pin 402 and the roof 414 of the eyelet pin 402 may simply have mating shapes such as a V-shaped groove and a V-shaped protrusion or a ball and socket.

In yet other embodiments, a plug or insert may be affixed to the roof of the eyelet 409 to provide better gripping. Such a plug or insert may have some of the aforementioned features. In other embodiments, the insert may comprise a high friction material, such as silicone having a high frictional coefficient or any combinations of any of the above-noted features. It may also be fabricated from a dissimilar metal from the remainder of the eyelet pin 403. In yet other embodiments, it may comprise a rubber bumper or a leaf spring.

In a preferred embodiment of the invention, the proximal end of insert 405 is rounded over or flared, as shown by reference 428 so as to eliminate any sharp edges from contacting the suture and possibly causing it to tear or break.

Exemplary Embodiments of Impactor Tool

Figure 46:
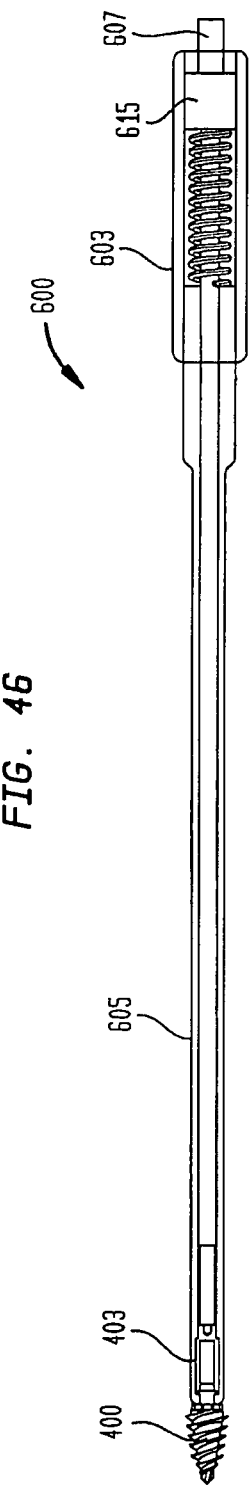
FIG. 46 is a semi-transparent side view of an impactor tool for driving the center pin of a bone anchor device of the present invention from the open position to the closed condition in the anchor main body of the bone anchor device.
Figure 47:
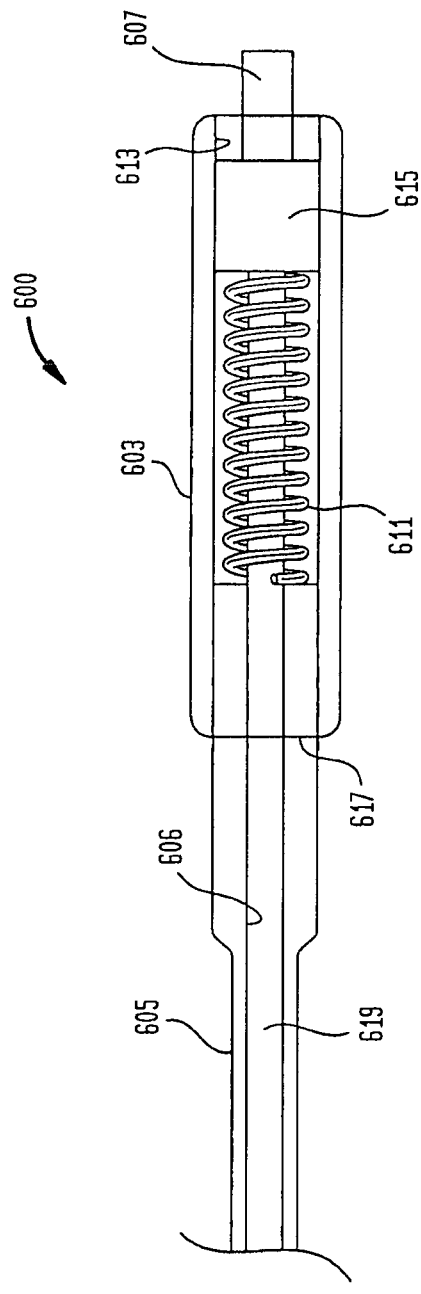
FIG. 47 is a close-up, semi-transparent view of the proximal end of the impactor tool of FIG. 46.
Figure 48:
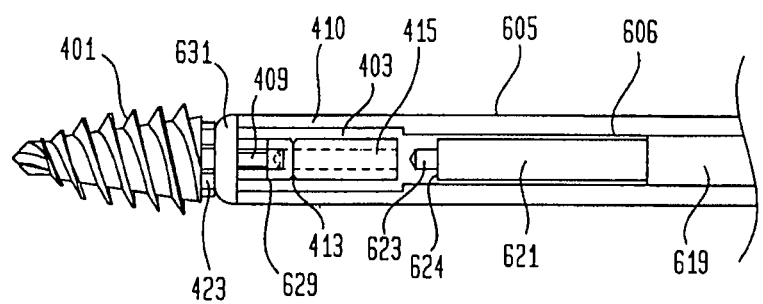
FIG. 48 is a close-up, semi-transparent view of the distal end of the impactor tool of FIG. 46.

FIGS. 46-48 show an exemplary impactor tool 600 that can be used in connection with the bone anchor device 400 in the procedure described above. FIG. 46 shows the entire tool. FIG. 47 shows a close up view of the proximal portion of the tool. FIG. 48 shows a close up view of the distal portion of the tool. Tool 600 comprises an elongated tube 605 having an internal through bore 606. The opening 629 at the distal end of the tube (best seen in FIG. 48) is sized to snugly accept the eyelet pin 403 therein, but not the anchor main body 401, as shown. A handle 603 having a bore 613 coaxial with the bore 606 of tube 605 is mounted to the proximal end of tube 605. Disposed inside the handle and tube is a rod 619 that is spring loaded by a spring 611 constrained in handle 603. The spring has light force so as to keep the proximal end 607 of the rod 619 extending completely through the handle 603 so that the proximal end 607 of is exposed such that it can be hit with a mallet or other impacting device. A block 615 is fixedly attached to the rod 619 near the proximal end 607, but trapped within the handle 603. Block 615 provides a stop for the spring 611, which is trapped between the block 615 and the distal end 617 of the handle 603. The spring 611 and block 615, when unbiased, maintain rod 619 in the shown position. Thus, striking end 607 of rod 619 drives the rod 619 down through the handle 603 and tube 605. Although not shown, an enlarged, more stable striking surface for the mallet may be provided either integral with proximal end 607 of rod 619 or as a separate piece that slidably fits over proximal end 607 of rod 619. The enlarged striking surface may be metal, plastic, or any other suitable material.

The distal end of the rod 619, as best seen in FIG. 48, includes a narrowed diameter portion 621 and an even smaller diameter portion (or pin) 623 at the distal end. Portions 623 and 621 are designed so that pin 623 will slidably but snugly fit within the proximal bore 415 of the eyelet pin 403 and the shoulder 624 between pin 623 and narrowed portion 621 will butt up against the proximal end of the eyelet pin 403 when spring 611 is sufficiently compressed. However, in the unbiased condition, as shown in FIGS. 46-48, pin 623 is not engaged in proximal bore 410 of eyelet pin 403, but is coaxial with but slightly spaced from bore 410. The aforementioned spring 611 maintains the rod in this spaced position from the bone anchor device. A bumper (or ring) 631, comprised, for instance, of silicone, is attached to the distal end of tube 605 having a hole 632 aligned coaxially with hole 629 in the end of tube 605. However, in other embodiments, pin 623 may be disposed in bore 410 with the shoulder 624 resting against the proximal end of the eyelet pin 403.

In operation, when it is time to drive the eyelet pin 403 from the open position illustrated in FIG. 36 to the closed position illustrated in FIG. 37, impactor tool 600 is slipped over the bone anchor device 400 as shown in FIG. 48. Particularly, bumper 631 is slid over the extension portion 410 of the eyelet pin 403 until it butts up against the head 423 of the anchor main body 401 of the bone anchor device 400. Any sutures (not shown in FIG. 48) passing through eyelet 409 in eyelet pin 403 would be temporarily held between the head 403 of the anchor main body 400 and the bottom of the bumper 631.

Since the bumper is soft, the sutures would be able to slide, upon being pulled by the surgeon between the head 423 and the bumper 631.

In use, after positioning the impactor tool over the eyelet pin extension portion 410 as shown in FIG. 48, the surgeon will grab the end of the suture or sutures through another cannula and pull to the desired tension, drawing the tissue into the desired position relative to the bone. The surgeon can then push the impactor tool 600 down on the top of the anchor main body 401 with some additional force, to hold the sutures in this tensioned state between the bottom of the bumper 631 and the top of the anchor main body 401. The surgeon can then let go of the sutures and the interaction between the bumper and the top of the anchor main body 403 will hold the sutures in this tensioned position, without damaging the sutures, until the surgeon can strike the impactor tool 600, causing the eyelet pin 403 to be driven downwardly into the closed position in which the sutures will be locked in the bone anchor device 400.

Specifically, when the surgeon strikes the proximal end 607 of the impactor tool 600, pin 623 descends into bore 415 and drives eyelet pin 403 down into anchor main body 401 to the closed position shown in FIG. 37. Particularly, the force of the impact being sufficient to force the second ramp formation 407 through locking ring 404 and to overcome the interference fit between central pin 402 and eyelet pin and distal bore 418 of eyelet pin 403). When ramp formation 407 passes distal surface 404a of locking ring 404, locking ring 404 returns elastically to its stress-free state against shaft 419 of eyelet pin 403.

Preferably, the diameter of the pin 623 is slightly larger than the diameter of the proximal bore 415 of the eyelet pin such that the pin 623 forms an interference fit inside the bore 415 at this time. Preferably, the interference fit is relatively weak so that the eyelet pin 403 can be removed from the impactor tool 600 at a later time.

When the eyelet pin 403 is in the open position, the V-groove 413 defining the breakaway portion 410 of the eyelet pin is preferably proximal to the bumper 631, as shown in FIG. 48. Accordingly, the soft bumper 631 and distal tip of cannula 605 helps unload the force of the impact from the V-groove 413 so as to help prevent it from accidentally breaking prematurely before or during impact.

After the eyelet pin 403 is driven down into the closed position, the impactor tool 600 is then used to break off the breakaway portion 410 of the eyelet pin 403. This is achieved by rocking the impactor tool (and the cannula within which it is inserted in an arthroscopic procedure) back and forth so that it pivots about the bumper 631 engaged with the top of the anchor main body 401. Particularly, when eyelet pin 403 is in the closed position, the V-groove 413 in the eyelet pin 403 is essentially even with the top of the anchor main body 401, and thus with the bottom of the bumper 631. The bumper permits the impactor tool 600 to be rocked back and forth so that the V-groove can be broken without metal to metal contact between the impactor tool 600 and the anchor main body 400. Once broken, the breakaway portion of the eyelet pin will stay inside the impactor tool because of the weak interference fit between the pin 523 at the end of the rod 619 pf the impactor tool 600 and the proximal bore 415 of the eyelet pin. Alternately or additionally, the hole 632 defined by the ring-shaped bumper may be designed to be slightly smaller than the diameter of the extension portion 410 of the eyelet pin so that the bumper must slightly deform radially outwardly when it is slipped over the extension 410 providing a tight, but still slidable fit with the extension 410. This would provide an alternative or additional means of retaining the breakaway portion 410 of eyelet pin 403 inside the impactor tool 600. The impactor tool 600 can then be removed with the breakaway portion 410 contained therein.

In other envisioned embodiments of the invention, a tool that is capable of delivering a precisely controlled striking force may be used instead of a simple mallet. The tool would be adapted to fit over the proximal end 607 of the rod 619 and to deliver a blow along the longitudinal axis of the rod 619. For instance, Applicants envision a spring-loaded tool, wherein the spring loading is released by a small tap of a mallet, the spring selected and pre-loaded to deliver the exact amount of force desired over the exact travel distance desired. This force should be sufficient to push ramp formation 406 or 407 through locking ring 404 as previously described, but not so much as to injure the bone. In other embodiments, the spring may be released by a trigger mechanism instead of a mallet.

Fifth Set of Exemplary Embodiments

Figure 42:
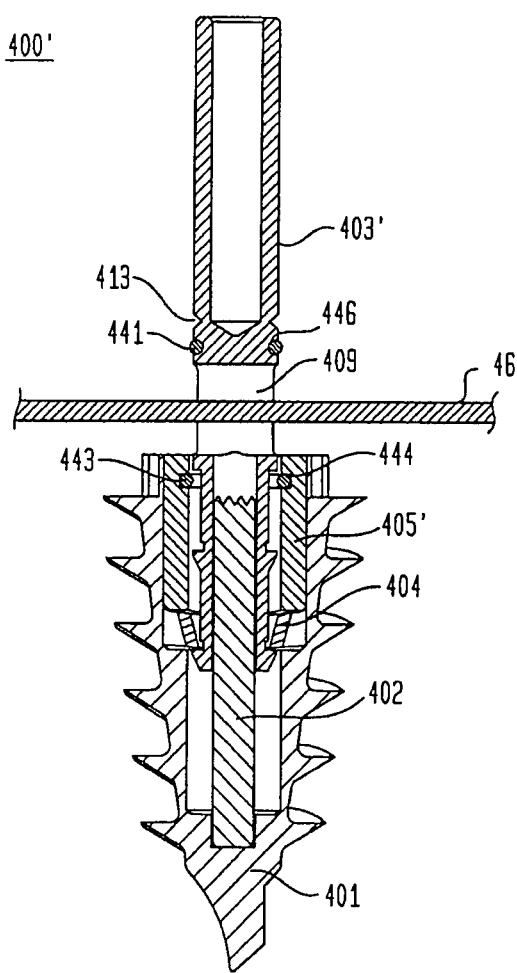
FIG. 42 shows a cross-sectional side view of a bone anchor device in the open state in accordance with a fifth embodiment of the invention.
Figure 43:
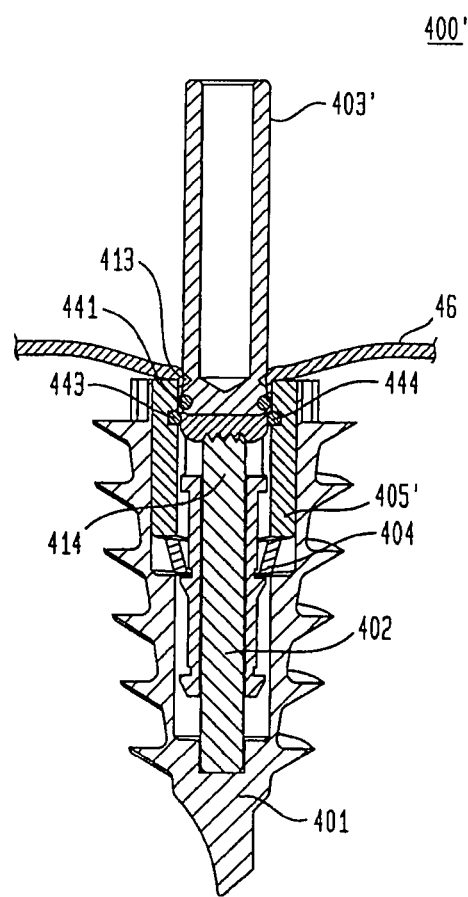
FIG. 43 is a cross-sectional side view of the bone anchor device of FIG. 42 in the closed state.

FIGS. 42 and 43 are cross-sectional views illustrating an alternative embodiment 400' to the bone anchor device 400 shown in FIGS. 36-41. FIG. 42 shows the bone anchor device 400' in the open position, while FIG. 43 shows it in the closed position. The device 400' is largely similar to device 400 shown in FIGS. 36-41. However, it includes two O-rings 443 and 441 that assist with suture management. Particularly, in this embodiment, the insert 405' is slightly modified from the insert 405 of FIGS. 36, 37 and 41. Particularly, it includes a groove 444 near its proximal end 405' within which a silicone or other resilient material O-ring 443 sits. In a similar manner, eyelet pin 403' also is adapted to have another groove 446 for accepting another O-ring 441 positioned just above the eyelet 409. As can be seen in FIG. 43, when in the closed position, O-rings 441 and 443 meet and press against each other near the top of the anchor main body 401, precisely where the suture 46 passes through the bone anchor device 400a. The soft material of the O-rings 441 and 443 grips the suture tightly and also prevents the suture from contacting metal at this juncture, thereby helping assure that the sutures are not damaged or broken during or after the eyelet pin is driven into the closed position. The O-rings may be formed of high friction silicone or any other reasonably resilient material.

In yet other embodiments of the invention, other features similar in shape and position to the O-rings 441 and 443 may be provided. Those features may be formed of materials other than the material of the eyelet pin 403 and/or insert 405. Alternately, the features may be formed directly into the eyelet pin 403' and/or insert 405'. The features should have rounded non-sharp shapes that help grip the suture without damaging it.

Sixth Set of Exemplary Embodiments

FIGS. 44A-44F illustrate further embodiments of the invention. For sake of clarity, only the eyelet pin 403 and the central pin 402 are shown in each of FIGS. 44A-44E. However, it should be understood that these components are disposed in the anchor main body 401 with the other elements, such as locking ring 404 and insert 405, but they are not shown in these Figures in order not to obfuscate the features being particularly illustrated in these Figures. The angle of view in FIGS. 44A-44D is rotated 90° from the angle of view in FIGS. 36 and 37.

Figure 44A:
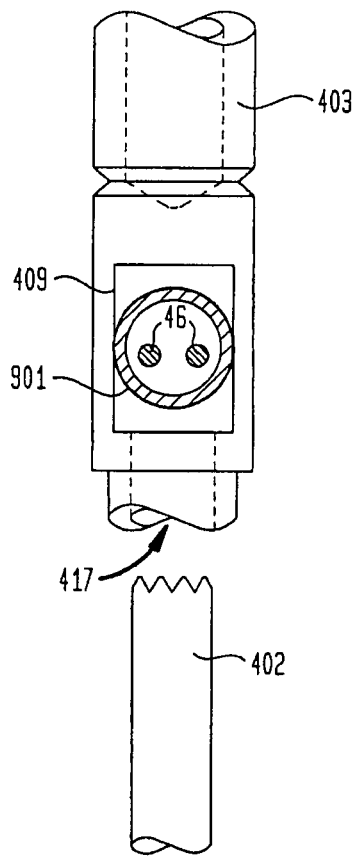
FIG. 44A shows a close-up view of the eyelet of the eyelet pin in accordance with a first alternate embodiment of the bone anchor device of FIG. 36 in the open state.
Figure 44B:
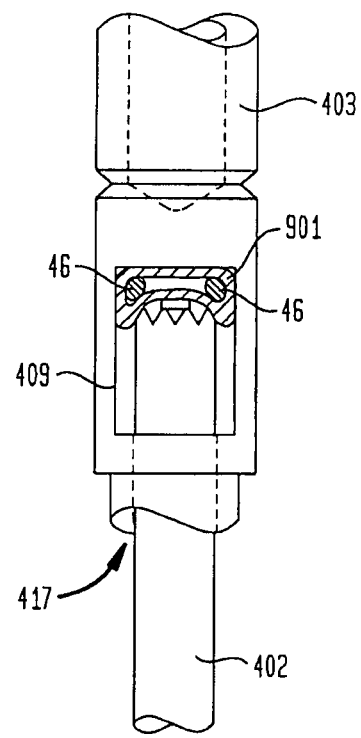
FIG. 44B shows a close-up view of the eyelet of the eyelet pin in accordance with the first alternate embodiment of the bone anchor device of FIG. 36 in the closed state.

FIG. 44A and 44B illustrate a first alternate embodiment of the bone anchor device 400 in which a hollow cylinder 901 is disposed in the eyelet 409. The hollow cylinder 901 is formed of a thin-walled deformable material, such as metal. In one embodiment, the material is plastically deformable. However, if it also could be elastically deformable. In the illustrated embodiment, the hollow cylinder 901 is circular and the eyelet 409 is square with the hollow cylinder 901 sized to have a diameter equal to the transverse cross-section of the eyelet 409. Therefore, the hollow cylinder 901 contacts the sides of the eyelet at two locations spaced 180° around the hollow cylinder 901. However, in other embodiments, the eyelet could be square so as to contact the eyelet at four locations spaced at 90° intervals around the hollow cylinder. According to even further embodiments, the hollow cylinder could be oval (and may or may not contact the eyelet at four locations spaced at 90° intervals around the hollow cylinder).

The sutures 46 that pass through the eyelet 409 pass through the middle of the hollow cylinder 901.

Referring now to FIG. 44B, which shows the condition of the components when in the closed position, when the eyelet pin 403 is driven down so that central pin 402 enters the eyelet 409 as previously described, it impinges upon the hollow cylinder 901, deforming it into the shape shown in FIG. 44B. As can be seen, the eyelet 409, hollow cylinder 901 and central pin 402 are sized relative to each other such that the sutures 46 are crushed by the hollow cylinder 901. In other words, the clearance between the central pin 402 and the sides of the eyelet 409 is less than the diameter of the suture such that the suture gets fixedly trapped or compressed. One or more sutures also may get fixedly trapped in between the proximal end 408 of the central pin 402 and the roof 414 of the eyelet 409.

This configuration may provide stronger gripping of the sutures.

Figure 44C:
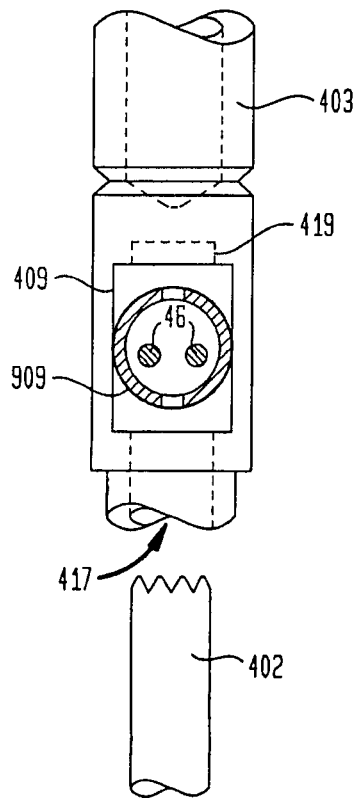
FIG. 44C shows a close-up view of the eyelet of the eyelet pin in accordance with a second alternate embodiment of the bone anchored device of FIG. 36 in the open state.
Figure 44D:
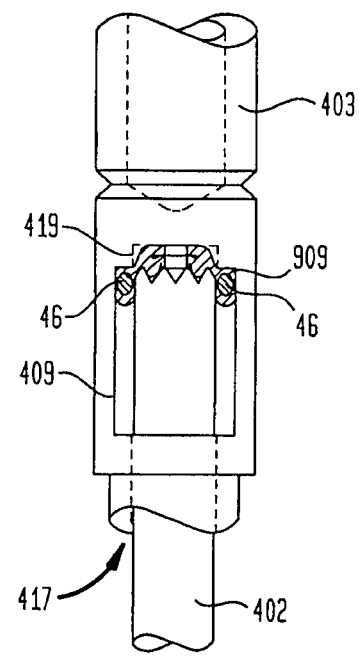
FIG. 44D shows a close-up view of the eyelet of the eyelet pin of the bone anchor device in accordance with the second alternate embodiment of FIG. 36 in the closed state.
Figure 44E:
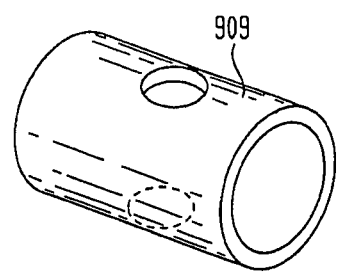
FIG. 44E shows a perspective view of the cylinder of the second alternative embodiment of FIGS. 44C and 44D separate from the overall device.
Figure 44F:
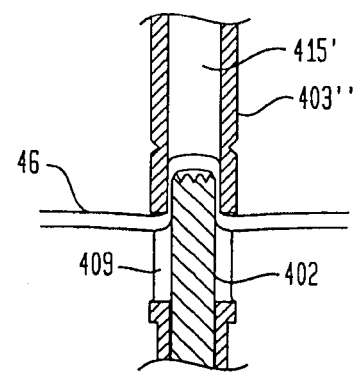
FIG. 44F shows a further embodiment of the eyelet pin of the bone anchor device in cross-section in the closed state.

FIGS. 44C, 44D, and 44E illustrate another alternate embodiment involving a modified cylinder 909. FIG. 44C shows this configuration in the open state and FIG. 44D shows it in the closed state. FIG. 44E shows a perspective view of the cylinder 909 disembodied from the device for sake of clarity. These Figures illustrate two alternate features relative to the device shown in FIGS. 44A and 44B that can be incorporated individually or in combination into the device. First, ring 909 has a hole 911 and optionally a second hole 912 formed therein coaxial with each other, and the ring 909 is inserted into the eyelet with the holes coaxially aligned with the distal bore 417 of the eyelet pin 403. Second, an opening 419 through which the central pin 402 can pass may exist in the roof or top wall 414 of the eyelet 409. Alternately, the proximal bore 415 may simply extend all the way to and in communication with the eyelet, thereby providing the opening in the top wall 414 of the eyelet. The holes 911, 912 are smaller than the central pin 402 such that the central pin cannot pass through eyelet without also deforming the holes 911, 912 as well as the ring 909 itself.

As shown in FIG. 44D, in this embodiment, when the central pin 402 is driven through the eyelet 409, it punches through the bottom hole 911, thereby deforming the cylinder 909 as shown and capturing the sutures inside the crushed ring 909. In addition, if an opening 419 is provided in the top wall 414 of the eyelet and/or a second hole 912 is provided in the ring 909, the central pin may punch through the top hole 912 and/or the opening 419. As in the embodiment of FIGS. 44A and 44B, the sutures become fixedly trapped above the proximal end 408 of the central pin in the ring 909 and/or in opening 419. In the embodiment of FIGS. 44C and 44D, at least those sutures that are located in opening 419 of the eyelet pin 403 take on an even more tortuous path, thereby providing even greater gripping of the sutures in the bone anchor device.

FIG. 44F shows an even further embodiment of the invention in which the proximal bore 415' of the eyelet pin 403" extends completely through and is in communication with the eyelet 409 such that there is a bore running continuously through the eyelet pin from the distal end, through the eyelet, and to the proximal end of the eyelet pin 403". In this embodiment, there is no surface in the roof of the eyelet 409 that the proximal end 408 of the central pin 402 can crush sutures up against. Nevertheless, sutures that do end up above the central pin 402, rather than on the sides thereof, take on a particularly tortuous path, and therefore are still tightly gripped in the bone anchor device.

The various different hollow cylinders 901, 909 and the various different configurations of the bore 415 and 417 in the eyelet pin 403 can be combined with each other in various permutations. For example the hollow cylinder 901 need not be a continuous ring and may have a circumferential gap (e.g., a split hollow cylinder) such as a rolled piece of thin metal or a roll pin.

In other embodiments, as already noted, the hollow cylinder need not be perfectly cylindrical, but can have an oblong or oval cross-section. In such embodiments, the eyelet can be rectangular so as to match the dimensions of an oval hollow cylinder (i.e., contacting it at four locations spaced 90° from each other around the circumference of the hollow cylinder) or it can have a square profile such that the hollow cylinder only contacts the eyelet at two location spaced 180° from each other around the circumference of the hollow cylinder.

In any of the embodiments discussed hereinabove in connection with the use of a hollow cylinder in the eyelet, it may be preferable to round out the proximal end of central pin 402 so as to avoid any sharp edges. This would help avoid the possibility of the central pain punching a hole through the hollow cylinder without substantially deforming it.

Seventh Set of Exemplary Embodiments

Figure 50:
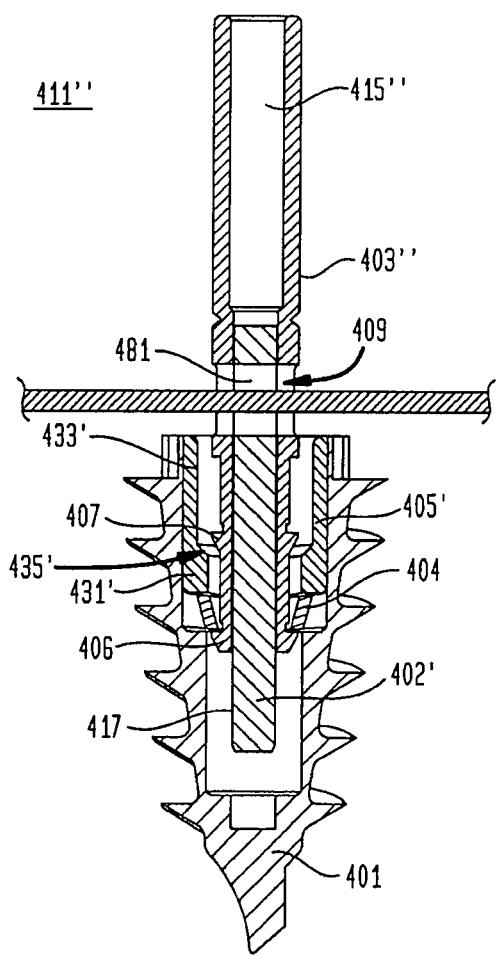
FIG. 50 shows a cross-sectional side view of a bone anchor device in the open state in accordance with a sixth embodiment of the invention shown.
Figure 51:
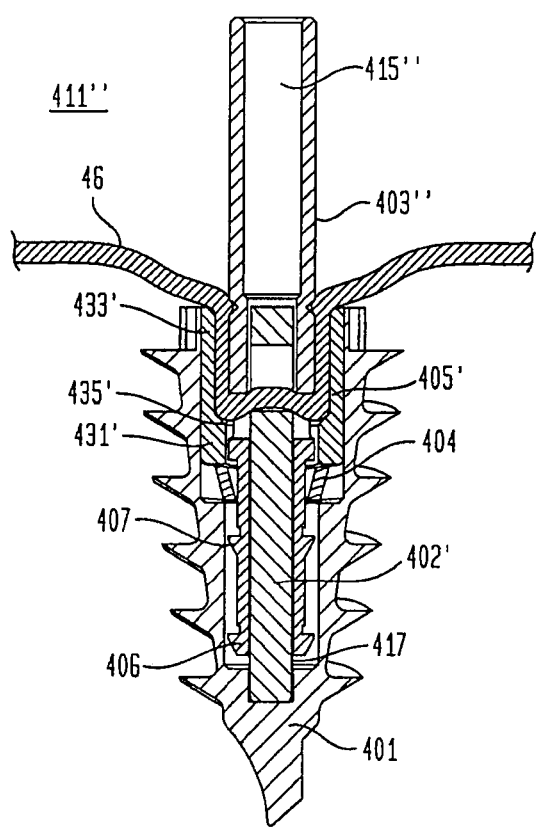
FIG. 51 shows a cross-sectional side view of a bone anchor device in the closed state in accordance with the sixth embodiment of the invention shown.

FIGS. 50 and 51 are cross-sectional views illustrating another alternative embodiment 400" to the bone anchor device 400 shown in FIGS. 36-41. FIG. 50 shows the bone anchor device 400" in the open position, while FIG. 51 shows it in the closed position. The device 400" is largely similar to device 400 shown in FIGS. 36-41. However, the eyelet pin 403", insert 405', and central pin 402' are modified, providing a different mechanism for fixing a suture 46 in the bone anchor device 400". Particularly, the significant modifications are as follows. First, central pin 402' includes its own eyelet 481 near its proximal end, which aligns with eyelet 409 in the eyelet pin 403" when in the open position, as shown in FIG. 50. Second, the proximal bore 415" in the eyelet pin 403" is slightly larger in diameter than the distal bore 417 and the central pin 402'. However, it should be noted that this is not necessarily a modification since the diameter of the proximal bore 415 relative to the distal bore 417 in the embodiment of FIGS. 36-41 was not specified. Also, the proximal bore 415" extends to and is in communication with eyelet 409 in the eyelet pin 403 (similarly to the embodiment of FIG. 44F). Insert 405 also is modified such that the shoulder 435' between the larger internal diameter of the proximal segment 433' and the smaller internal diameter of the distal segment 431' is lower. Although, again, this is not necessarily a modification since the position of shoulder 435 between the larger internal diameter of the proximal segment 433 and the smaller internal diameter of the distal segment 431 of the insert 405 in the embodiment of FIGS. 36-41 was not specified.

In this embodiment, the suture becomes locked in the device 400" by means of the two eyelets 409 and 481 shifting in longitudinal position relative to each other. Particularly, in the open position, the eyelet 481 in the central pin in longitudinally aligned (and also rotationally aligned about the longitudinal axis) with the eyelet 409 in the eyelet pin so that one or more sutures may pass through the eyelets 409, 481 essentially as described in connection with the embodiment of FIGS. 36-41. Then, when the eyelet pin is driven downwardly, the central pin moves downwardly until it bottoms out in the bottom of distal segment 418c of bore 418 in anchor main body 401, whereupon the force imparted to eyelet pin 403" overcomes the force of the interference fit between the central pin 402' and the distal bore 417 of eyelet pin 403" as well as forces ramp formation 407 past locking ring 404 and into the closed position. This causes the eyelet 409 in the eyelet pin 403" to move downwardly relative to the eyelet 481 in the central pin 402'. It can be seen in FIG. 51 that, in the closed position, the resulting longitudinal misalignment of the two eyelets 481 and 409 causes any suture(s) passing through the eyelets to take on a tortuous path and to become compressed and locked to the bone anchor device 400" at four separate locations. The first two are two of the same locations as in the embodiment of FIGS. 36-41, namely, at opposite ends 409a and 409b of the eyelet 409 between the outer surface 416 of the eyelet pin and the proximal section 433' of the insert 405'. The other two are between the surface of the central pin 402' and the proximal bore 415" of the eyelet pin 402", as indicated at 463 in FIG. 51.

It now should be apparent that the reason the proximal bore 415" is preferably slightly larger than the distal bore 417 proximal bore and the central pin 402' is to provide clearance for the sutures between the two. It also should now be apparent that the reason the shoulder 435' in the insert preferably is lower than in the embodiment of FIGS. 36-41 also is to provide sufficient clearance for the suture(s) between the insert inner bore and the surface 416 of the eyelet pin 416. More particularly, in this embodiment, because there must be room in the portion of the eyelet pin 403" above the eyelet 409 to accommodate both the eyelet 481 of the central pin 402' and a portion of the pin 402' above the eyelet 481 while still preferably maintaining the breakaway V-groove 413 essentially flush with the top of the anchor main body 401 in the closed position, the eyelet 409 in the eyelet pin 403" preferably is positioned lower into the anchor main body 401 when in the closed position than in the embodiment of FIGS. 36-41. Of course, these particular modifications are merely exemplary insofar as different sets of modifications may be implemented to achieve similar goals.

This embodiment provides secure fixing of the suture(s) in the bone anchor device In these types of embodiments, the bone anchor device could even possibly be delivered to the surgeon already in the closed state with or without one or more sutures already disposed in and passing through the eyelet.

Conclusion

As mentioned earlier, the exact configurations of the bone anchor devices are greatly variable, particularly within the parameters hereinabove described. Individual devices thus can be associated with particular predetermined features that will render them most effective for performing specific procedures. Also it should be noted that many of the features described in connection with individual embodiments of the present invention may be substituted into one or more of the other embodiments described herein, there being no limitation other than logic and physical limitations as to how the various features can be mixed and matched in a single device.

The same is true for the surgical procedures disclosed herein, i.e., certain aspects of certain of the described surgical procedure embodiments may be used in other described surgical procedure embodiments described herein and/or may be performed in connection with other embodiments of the bone anchor devices and/or time fastener devices than those used in the exemplary embodiments described herein.

The procedures and medical devices as described can be altered in various further ways while still accomplishing the same results and the invention also covers such variations in the procedure.

It is submitted that, with the use of the present invention, the arthroscopic rotator cuff repair procedure is significantly facilitated by the use of the bone anchor device and/or the tissue fastener device of the present invention.

It must be understood in the above regard that one of the biggest challenges in arthroscopic surgery is knot tying. It is technically challenging and, insofar as the use of the bone anchor devices and/or the tissue fastening devices of the invention facilitate knotless suture fixation, the challenges associated with knot tying are largely overcome.

It must also be understood in the above regard that another challenge in arthroscopic surgery is suture management. It is technically challenging and, insofar as the use of the medical device of the invention facilitates effective suture management and loading of the suture anchor, the challenges associated with suture management are largely overcome.

Although other knotless fixation devices are already known, some of these require an anchor body to which a suture must be anchored to be located in a pilot hole. It is technically challenging to place an anchor body into the pilot hole, particularly because the hole often bleeds, obscuring the hole and, even if the hole does not bleed, recreating the exact angle that was used during the creation of the pilot hole is sometimes difficult. Placement of cannulas directly over a pilot hole also may create a suction effect dragging soft tissue over the hole, further obscuring it. It is thus often time-consuming and frustrating to locate the hole and correctly locate the bone anchor device in the hole. Incorrect angular location of an anchor device in a hole may occur from the precise angle of insertion necessary for good bone purchase and this may result in failure of some of the known knotless fixation devices. The procedures associated with the self drilling and self tapping bone anchor devices of the present invention as above described alleviate the problem of finding a pilot hole for a bone anchor device. Insofar as the use of other known knotless fixation devices and generally anchor devices may be associated also with various other problems and difficulties, either generally or specifically in relation to specific devices, the use of the medical device of the invention may serve also to at least alleviate these problems and difficulties.

It is also known that all presently available anchor designs are "buried" below the bone. This is done to prevent impingement of the head of the device with surrounding anatomy. Although the medical device of the invention may use a body with either no head or a lower profile head that allows the body to be buried below the bone, there are distinct advantages to using an anchor main body having a head that remains accessible externally of the humerus. As such, the anchor main body can be easily unscrewed from the humerus. With respect to some embodiments described herein, it is also possible to pull the eyelet pin from its anchor main body. The above may be necessary where a repair has failed and/or is not satisfactory and needs to be removed, where inadvertent suture dislodgement from the anchor device has occurred where irreversible tanglement of sutures has occurred, and/or where a suture knot comes loose. It is envisaged in this regard that bone anchor devices in accordance with the invention may be provided with anchor main bodies of larger diameter for placement in original holes formed by removed anchor main bodies to provide for optimal purchase strength of the device to bone. The use of the bone anchor device of the invention, therefore, reduces or eliminates the need, in the circumstances described above, for placing additional anchors within the limited space available for a repair, additional bone anchors may induce the risks of confluence of anchor holes, bone fracture and/or anchor pull-out. It must also be understood in relation to the use of known anchor devices, that at times the devices can be removed only by coring techniques that are cumbersome and time consuming and that often lead to significant bone loss that requires bone grafting. Bone grafting in itself may be associated with problems, thus rendering the use of the medical device of the invention significantly more appropriate in relation to many different procedures, when compared with the use of known anchoring techniques and anchoring devices, even known knotless fixation devices.

It is thus submitted that the known problems associated with the tying of sutures, the management of sutures and also the anchoring of sutures to the humerus, are largely alleviated, the same applying also in relation to other procedures with which the medical device of the invention can be conveniently used, either arthroscopically, or otherwise.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A bone anchor device comprising:
a main anchor body defining a longitudinal axis and having an external formation for engaging the main anchor body to a bone and a receiving formation; and
an eyelet pin defining a longitudinal axis and having a passage substantially transverse to the longitudinal axis through which a length of suture can be threaded;
wherein the eyelet pin is longitudinally insertable in the receiving formation from an open position, in which a suture passing through the eyelet would not be fixed in the passage and may translate within the passage, into a closed position, in which a suture passing through the passage in the eyelet pin would be fixed in the passage; a central pin disposed in the receiving formation and having a longitudinal axis parallel to the longitudinal axis of the main body, the central pin having a proximal end and a distal end; and wherein the eyelet pin has a proximal end and a distal end and includes a distal longitudinal bore running between and open to each of the transverse passage and the distal end of the eyelet pin and wherein the interaction between the distal longitudinal bore of the eyelet pin and at least a portion of the central pin form an interference fit.

2. The bone anchor device of claim 1 further comprising at least one suture threaded through the passage in the eyelet pin, and wherein, in the device's preoperative state, the eyelet pin is partially inserted in the receiving formation defined by the anchor main body in the open position.

3. The bone anchor device of claim 2 wherein, in the open position, the passage in the eyelet pin is exposed outside of the anchor main body.

4. The bone anchor device of claim 1 further comprising at least one suture threaded through the passage in the eyelet pin, and wherein, in the device's pre-operative state, the eyelet pin is in the closed position in the receiving formation.

5. The bone anchor device of claim 1 wherein the central pin and eyelet pin are freely rotatable about their longitudinal axes relative to the main anchor body.

6. The bone anchor device of claim 1 wherein the eyelet pin is translatable relative to the central pin along their respective longitudinal axes from the open position to the closed position, in which closed position the proximal end of the central pin extends into the transverse passage in which a suture in the passage would be trapped between the central pin and the eyelet pin.

7. The bone anchor device of claim 6 further comprising a suture in the passage and wherein the transverse passage has a top wall and a clearance between the proximal end of the central pin and the top wall of the transverse passage when the device is in the closed position, the clearance being less than a diameter of the suture in the passage.

8. The bone anchor device of claim 7 wherein at least one of the proximal end of the central pin and the top wall of the transverse passage includes formations to assist in gripping a suture trapped therebetween.

9. The bone anchor device of claim 1 further comprising:
a locking ring captured in the receiving formation and having an inner diameter and an outer diameter;
wherein the eyelet pin further comprises at least a first ramp formation on an outer surface thereof defining a diameter greater than the inner diameter of the locking ring when in an unbiased state, the first ramp formation adapted to cooperate with the locking ring to capture the eyelet pin in the main anchor body.

10. The bone anchor device of claim 9 wherein the first ramp formation is adapted to impart a spreading force on the locking ring when the eyelet pin is driven distally into the receiving formation whereby, upon application of sufficient force for the first ramp formation to bias the locking ring to a diameter greater than the diameter defined by the first ramp formation, the first ramp formation can traverse the locking ring to a position distal of the locking ring, whereupon the locking ring will return to its unbiased state.

11. The bone anchor device of claim 10 wherein, in the preoperative state, the first ramp formation is positioned distal of the locking ring.

12. The bone anchor device of claim 11 wherein the locking ring has a frustoconical inner wall adapted to cooperate with the first ramp formation to convert longitudinal movement of the eyelet pin relative to the locking ring into radially outward force on the locking ring.

13. The bone anchor device of claim 12 wherein the eyelet pin further comprises a second ramp formation on the outer surface thereof proximal of the first ramp formation and defining a diameter greater than the inner diameter of the locking ring when in an unbiased state, the second ramp formation positioned such that, when the device is in the preoperative state, the second ramp formation is proximal of the locking ring, and, when the device is in the postoperative state, the second ramp formation is distal of the locking ring.

14. The bone anchor device of claim 9 wherein the receiving formation of the anchor main body further comprises an insert within the receiving formation comprising a hollow cylinder and forming an interference fit in the receiving bore proximal of the locking ring, the insert having an inner diameter smaller than an outer diameter of the locking ring over at least a portion of the insert, wherein the insert captures the locking ring in the receiving formation.

15. The bone anchor device of claim 1 further comprising a suture shuttle disposed through the transverse passage, wherein the suture shuttle comprises an elongated flexible member having first and second ends.

16. The bone anchor device of claim 15 wherein the elongated flexible member comprises a wire.

17. The bone anchor device of claim 16 wherein the wire is metal.

18. The bone anchor device of claim 15 wherein the elongated flexible member comprises a filament.

19. The bone anchor device of claim 18 wherein the filament is made from a polymer.

20. The bone anchor device of claim 15 wherein the flexible member further comprises a loop formed on at least one end.

* * * * *